US012716885B2

(12) United States Patent
Chen et al.

(10) Patent No.: US 12,716,885 B2
(45) Date of Patent: Aug. 25, 2026

(54) SYSTEMS FOR FORMING A NANOPORE IN A LIPID BILAYER

(71) Applicant: Roche Sequencing Solutions, Inc., Pleasanton, CA (US)

(72) Inventors: Roger J.A. Chen, Saratoga, CA (US); Randall Davis, Pleasanton, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 119 days.

(21) Appl. No.: 18/933,460

(22) Filed: Oct. 31, 2024

(65) Prior Publication Data

US 2025/0123264 A1 Apr. 17, 2025

Related U.S. Application Data

(60) Continuation of application No. 18/471,506, filed on Sep. 21, 2023, now Pat. No. 12,158,462, which is a continuation of application No. 17/445,180, filed on Aug. 16, 2021, now Pat. No. 11,768,195, which is a division of application No. 16/516,166, filed on Jul. 18, 2019, now Pat. No. 11,092,589, which is a continuation of application No. 15/488,432, filed on Apr. 14, 2017, now Pat. No. 10,371,692, which is a continuation of application No. 14/150,322, filed on Jan. 8, 2014, now Pat. No. 9,678,055, which is a continuation-in-part of application No. 12/658,591, filed on Feb. 8, 2010, now Pat. No. 9,605,307.

(51) Int. Cl.

| | |
|---|---|
| ***G01N 33/487*** | (2006.01) |
| ***B81B 1/00*** | (2006.01) |
| ***G01N 15/12*** | (2006.01) |
| ***G01N 15/13*** | (2024.01) |
| ***G01N 33/483*** | (2006.01) |
| *B82Y 5/00* | (2011.01) |
| *C12Q 1/6869* | (2018.01) |

(52) U.S. Cl.

CPC ......... *G01N 33/48721* (2013.01); *B81B 1/00* (2013.01); *G01N 15/12* (2013.01); *G01N 15/13* (2024.01); *G01N 33/483* (2013.01); *B82Y 5/00* (2013.01); *C12Q 1/6869* (2013.01)

(58) Field of Classification Search

None

See application file for complete search history.

*Primary Examiner* — Benjamin A Schiffman

(74) *Attorney, Agent, or Firm* — FisherBroyles, LLP; Jason M. Pass; Frank W. Leak, Jr.

(57) ABSTRACT

A method of forming a nanopore in a lipid bilayer is disclosed. A nanopore forming solution is deposited over a lipid bilayer. The nanopore forming solution has a concentration level and a corresponding activity level of pore molecules such that nanopores are substantially not formed un-stimulated in the lipid bilayer. Formation of a nanopore in the lipid bilayer is initiated by applying an agitation stimulus level to the lipid bilayer. In some embodiments, the concentration level and the corresponding activity level of pore molecules are at levels such that less than 30 percent of a plurality of available lipid bilayers have nanopores formed un-stimulated therein.

9 Claims, 14 Drawing Sheets

SYSTEMS FOR FORMING A NANOPORE IN A LIPID BILAYER

CROSS REFERENCE TO OTHER APPLICATIONS

This application is a continuation of U.S. patent application Ser. No. 18/471,506, filed Sep. 21, 2023 which is a continuation of U.S. patent application Ser. No. 17/445,180, filed Aug. 16, 2021, now U.S. Pat. No. 11,768,195, which is a divisional application of U.S. patent application Ser. No. 16/516,166, entitled SYSTEMS FOR FORMING A NANOPORE IN A MEMBRANE, filed Jul. 18, 2019, now U.S. Pat. No. 11,092,589, which is a continuation of U.S. patent application Ser. No. 15/488,432, entitled SYSTEMS AND METHODS FOR FORMING A NANOPORE IN A LIPID BILAYER, filed Apr. 14, 2017, which is a continuation of U.S. patent application Ser. No. 14/150,322, now U.S. Pat. No. 9,678,055, entitled METHODS FOR FORMING A NANOPORE IN A LIPID BILAYER, filed Jan. 8, 2014, which is continuation in part of U.S. patent application Ser. No. 12/658,591, now U.S. Pat. No. 9,605,307, entitled SYSTEMS AND METHODS FOR FORMING A NANOPORE IN A LIPID BILAYER, filed Feb. 8, 2010, each of which are incorporated herein by reference for all purposes.

BACKGROUND OF THE INVENTION

Nanopore membrane devices having pore size in the order of 1 nanometer in internal diameter have shown promise in rapid nucleotide sequencing. When a voltage potential is applied across the nanopore immersed in a conducting fluid, a small ion current due to conduction of ions across the nanopore can be observed. The size of the current is sensitive to the pore size. When a molecule such as a DNA or RNA molecule passes through the nanopore, it can partially or completely block the nanopore, causing a change in the magnitude of the current through the nanopore. It has been shown that the ionic current blockade can be correlated with the base pair sequence of the DNA molecule.

However, this technology still faces various challenges and so far it has not been able to discriminate down to a single base pair. In particular, the electrical potential needed to attract a ssDNA molecule in the nanopore tends to cause the ssDNA molecule to pass through the nanopore very quickly, making analysis difficult. To solve this problem, attempts have been made to tether the ssDNA to a bead to arrest the movement of the ssDNA molecule through the nanopore. However, such an approach may involve extensive sample preparation and may not be suitable for small sample sizes. Improved techniques for DNA analysis using nanopore membrane devices are needed.

BRIEF DESCRIPTION OF THE DRAWINGS

Various embodiments of the invention are disclosed in the following detailed description and the accompanying drawings. Note that the figures are intended to illustrate the various embodiments of the present invention and they are not necessarily drawn to scale.

DETAILED DESCRIPTION

Figure 1:
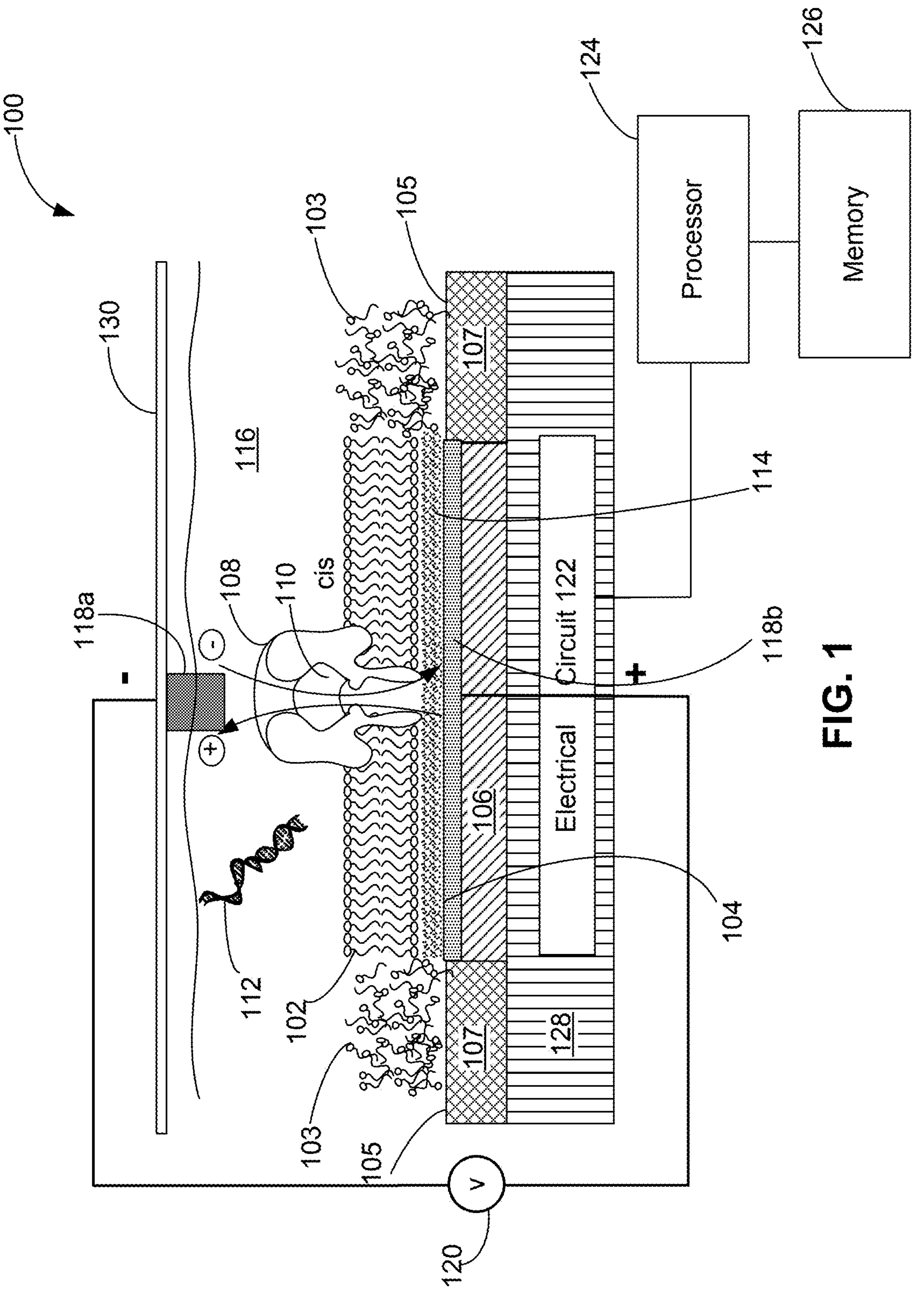
FIG. 1 is a schematic diagram of an embodiment of a nanopore device comprising a nanopore-containing a lipid bilayer.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims, and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Techniques for manipulating, detecting, characterizing, correlating and/or determining a molecule using a nanopore device are described herein. In one example, an acquiring electrical stimulus is applied across a nanopore-containing lipid bilayer characterized by a resistance and capacitance, where the acquiring electrical stimulus is of a level that tends to draw the molecule from a surrounding fluid into the nanopore. A change is detected in the electrical characteristics of the lipid bilayer resulting from the acquisition of at least a portion of the molecule into the nanopore. In response, the electrical stimulus level is changed to a holding electrical stimulus level. Typically, the level of the acquiring electrical stimulus that tends to draw a molecule from a surrounding fluid into the nanopore also tends to cause the molecule to progress through the nanopore too quickly. In order to trap the molecule in the nanopore for further detailed characterization, the electrical stimulus level often needs to be quickly reduced to a lower holding electrical stimulus level after detecting a change in the electrical characteristics of the nanopore containing lipid bilayer resulting from the acquisition of at least a portion of the molecule into the nanopore.

After the molecule is trapped in the nanopore, a progression electrical stimulus (e.g., a variable electrical stimulus) is then applied across the nanopore-containing lipid bilayer until the molecule progresses through the nanopore. The progression electrical stimulus level is such that it allows the molecule to progress through the nanopore in a fashion that allows recording of useful electrical signature(s) of the molecule for characterization. In some embodiments, the progression electrical stimulus level is lower than that of the acquiring electrical stimulus and higher than that of the holding electrical stimulus. As the molecule progresses through the nanopore, one or more electrical signature(s) of the molecule is recorded. The molecule can then be characterized based on the detected electrical signature(s).

A reverse progression electrical stimulus may also be applied to allow the molecule to reverse progress or rewind through the nanopore. The reverse progression electrical stimulus may be applied before, after and/or interspersed with the progression electrical stimuli. By cycling the progression electrical stimuli and the reverse progression electrical stimuli, repeat measurements of the molecule can be obtained during molecule progression and/or reverse progression through the nanopore. In some embodiments, the cycling is applied to a selected region of the molecule, such as a SNP site, a copy number variation site, a methylated site, a protein binding site, an enzyme binding site, a repetitive sequence site, and a restriction enzyme site to allow finer measurements, and better accuracy for the selected region of the molecule. In one example, a progression electrical stimulus may be applied first, followed by a reverse progression electrical stimulus, which is then followed by another progression electrical stimulus. By repeating measurements for the same portion of a molecule, an improved signal to noise ratio for measurements can be achieved. In one example, a plurality of reverse progression electrical stimuli is interspersed with a plurality of progression electrical stimuli, where each of the plurality of progression electrical stimuli is followed by a reverse progression electrical stimulus. In some embodiments, the polarity of the reverse electrical stimulus level is reversed compared to the progression electrical stimulus, and the reverse electrical stimulus pulls the molecule in a reverse progression direction. In some embodiments, the reverse electrical stimulus has the same polarity but a smaller magnitude (or a magnitude of zero) compared to the progression electrical stimulus and the natural tendency of the molecule to reverse progress through the nanopore pulls the molecule in the reverse progression direction. In such cases, the reverse electrical stimulus may serve to slow down the reverse progression of the molecule through the nanopore. The electrical signature(s) detected during the reverse progress can also be used to characterize the molecule. Under certain circumstances, the molecule can move in a more predictable and/or slower speed when it reverse progresses through the nanopore and the electrical signature(s) recorded may have better quality and signal to noise ratio. In one example, the molecule being characterized is a dsDNA molecule and when a reverse progression electrical stimulus is applied, the unzipped ssDNA molecules re-anneal to form a dsDNA molecule as it reverse progresses through the nanopore. In this example, the reverse progression electrical stimulus has the same polarity but a smaller magnitude than the progression electrical stimulus. The natural tendency of the unzipped ssDNA molecules to re-anneal to form a dsDNA molecule drives the molecule in the reverse progression direction. The reverse progression electrical stimulus acts to slow down the speed at which the DNA molecule reverse progresses through the nanopore. In the case where the reverse progression electrical stimulus has the same polarity as the progression electrical stimulus, an increase in the magnitude of the reverse progression electrical stimulus slows down the reverse progression of the molecule. In the case where the reverse progression electrical stimulus has the opposite polarity as the progression electrical stimulus, an increase in the magnitude of the reverse progression electrical stimulus speeds up the reverse progression of the molecule. In the example where the ssDNA re-anneal to form a dsDNA as the DNA molecule reverse progresses through the nanopore, the tendency for the ssDNA molecules to re-anneal to form the dsDNA (e.g., the energy released when the ssDNA molecules re-anneal to form the dsDNA) may affect the polarity and/or the magnitude of the reverse progression electrical stimulus. In other examples where a molecule re-hybridize with a hybridization marker as the molecule reverse progresses through the nanopore, the tendency for the molecule to re-hybridize with the hybridization marker (e.g., the energy released when the molecule re-hybridize with the hybridization marker) may affect the polarity and/or the magnitude of the reverse progression electrical stimulus.

The molecule being characterized using the techniques described herein can be of various types, including charged or polar molecules such as charged or polar polymeric molecules. Specific examples include ribonucleic acid (RNA) and deoxyribonucleic acid (DNA) molecules. The DNA can be a single-strand DNA (ssDNA) or a double-strand DNA (dsDNA) molecule. Other examples include polypeptide chain or protein.

The molecule can be modified prior to analysis. For example, the molecule can be hybridized with a hybridization marker prior to analysis. The hybridization marker may be anything that can bind to the molecule being characterized. The hybridization marker may serve to modify the energy (e.g., voltage level) required to move the molecule through the nanopore and/or may change the electrical signature of the molecule as it is threaded through the nanopore, by for example affecting the conformation of the molecule being characterized, the energy required to tear the molecule being characterized apart from the hybridization marker in order to thread the molecule through the nanopore, the energy released when the molecule is rehybridized with the hybridization marker. It should be noted that the hybridization marker may or may not necessarily move through the nanopore with the molecule being characterized. Examples of the hybridization marker include DNA, RNA, modified DNA, modified RNA, ligand, polymer, vitamin, fluorescent molecule, beads. For example, in cases where the molecule being characterized comprises a nucleotide molecule (e.g., DNA molecule), the hybridization marker can include a strand of nucleotide sequence (e.g., DNA or RNA sequence) or modified nucleotide sequence (e.g., modified DNA or RNA sequence) that complements the entire nucleotide molecule being characterized or a region of interest of the nucleotide molecule being characterized. The hybridization marker can for example include a nucleotide sequence that complements the nucleotide sequence of a single-nucleotide polymorphism (SNP) site, a copy number variation site, a methylated site, a protein binding site, an enzyme binding site, a repetitive sequence site, a restriction enzyme site, miRNA site, siRNA site, tRNA site, a transposon site, a centromere site, a telomere site, a translocation site, an insertion site, or a deletion site.

The electrical stimulus described herein can be various electrical stimuli, such as an applied current and an applied voltage. The current can be a direct current (DC) and/or an alternating current (AC). The electrical stimulus can constitute a series of electrical pulses.

The electrical signature may include any measurable electrical property of the nanopore, lipid bilayer, or nanopore-lipid bilayer system that changes as the molecule progresses through the nanopore that is indicative of the molecule's properties or structure. For example, different individual base pairs of a DNA molecule or sequences of base pairs may cause the nanopore to have different ionic current flow or resistance. Also, more or less voltage may be required to move a trapped DNA molecule through the nanopore because of different bonding strength between different base pairs of the DNA molecule. The bonding strength between different base pairs of the DNA molecule can be made larger or smaller by hybridizing the DNA molecule to different hybridization marker. Therefore, in various embodiments, the electrical signature may include instantaneous measurements or measurements made over time of voltage, resistance, and/or current profile across the lipid bilayer. For example, the electrical signature may include the magnitude(s) of the variable electrical stimulus required to affect the progression of the molecule through the nanopore. The electrical signature may also be a combined electrical signature combining electrical signatures of various discrete portions or frames of the molecule as it progresses through the nanopore. For example, characterizing the DNA molecule may be based on a combined electrical signature combining electrical signatures for various frames of the DNA molecule, each frame corresponding to an electrical signature of region of the DNA molecule (e.g., 1 to 20 base sequence) as the molecule threads through the nanopore under an applied electrical stimulus. In some embodiments, electrical signatures of one or more overlapping frames of a molecule may be combined and deconvolved to produce the electrical signature of the molecule. Overlapping the sampling frames may allow for a more accurate characterization of the molecule.

In some embodiments, in order to gather more data that may be used to characterize a molecule, multiple electrical measurements of the molecule may be acquired under the same or different chemical or environmental conditions. Multiple electrical measurements of the same molecule may be achieved by repeatedly rewinding the molecule through the nanopore and repeating the electrical measurements under the same or different conditions. In some embodiments, different chemical or environment conditions may be achieved by varying one or more of various environmental variables, such as pH, salt concentration, glycerol concentration, urea concentration, betaine concentration, formamide concentration, temperature, divalent cation concentration, and other environmental variables. The repeat measurements can be carried out in a single experiment to the same molecule or in different experiments to the same molecule or different molecules. The repeat measurements may be carried out by rewinding the molecule in the nanopore under an applied reverse progression electrical stimulus. In some embodiments, the repeat measurements may be carried out for one or more regions of interest of the molecule, such as single nucleotide polymorphism (SNP) sites and methylated sites of a DNA molecule. In some embodiments, the molecule being characterized may assume different conformations and/or orientations as it is drawn through the nanopore, causing the measured electrical signature(s) of the same molecule to differ from experiment to experiment and making it difficult to characterize the molecule. By repeatedly measuring the electrical signature(s) of the same molecule, usually under the same conditions, and obtaining a library of unique electrical signatures of the molecule from the repeat measurements, the different signatures from the different conformations and/or orientations of the molecule can be used to cross-check and increase the confidence in identifying a particular biomarker.

Characterization of the molecule can include determining any property of the molecule that causes a variance in a measurable electrical signature. For example, a base sequence of an DNA molecule may be derived from measuring a variance in ionic current flow (or electrical resistance) through the nanopore as the DNA molecule progresses through the nanopore, and/or from measuring the voltage required to pull at least a portion of the molecule (e.g., a single strand of a dsDNA molecule) through the nanopore at various points of the molecule. If the molecule being characterized is a dsDNA, characterizing the molecule may include identifying one or more GC and/or AT base pairs of the dsDNA molecule. Characterization of the molecule can also include determining a property of the molecule by comparing and correlating the measured electrical signature(s) of the molecule with electrical signature(s) of known molecules to obtain a possible structure of the molecule. For example, the base sequence of a segment of a DNA molecule can be determined by comparing and correlating the measured electrical signature(s) of the DNA molecule with electrical signature(s) of known DNA segments. In some embodiments, the molecules being characterized are DNA segments of a gene. The sequences of the DNA segments determined using the techniques described herein can be used for de novo sequencing of the gene. In one example, the gene being sequence may be fragmented into shorter nucleotide sequences (e.g., 50 to 10,000 base pairs) using one or more restriction enzymes. Sequences of individual DNA segments may be determined by correlating the detected electrical signature(s) of the DNA segment with that of known DNA sequences. The entire sequence of the genome can then be reconstructed by aligning overlapping portions of the fragmented DNA segments.

The herein described techniques for manipulating and characterizing a molecule may be highly sensitive and may not require extensive sample treatment, such as amplification, separation, and derivatization, thus very small amount of sample may be needed. This makes the techniques described herein especially suitable for applications that require high sensitivity and/or offer limited sample size. Examples of such applications include cancer biomarker screening, infectious disease detection, newborn screening, and bioterrorism agent screening.

Additionally, techniques for assembling a lipid bilayer on a substantially planar solid surface are described herein. The lipid bilayer compatible surface may be isolated by one or more lipid bilayer incompatible surfaces that are not suitable for forming a lipid bilayer. The lipid bilayer incompatible surfaces may limit the size of the lipid bilayer formed to the edges of the lipid bilayer compatible surfaces since the lipid bilayer only forms on lipid bilayer compatible surfaces and does not form on lipid bilayer incompatible surfaces. In one example, a lipid suspension (e.g., aqueous electrolyte solution containing suspended lipid colloids) is deposited over the lipid bilayer compatible surface as well as the adjacent lipid bilayer incompatible surfaces. In some embodiments, the lipid bilayer compatible surface comprises a hydrophilic material. Any materials that tend to allow formation of a lipid bilayer may be used. In some embodiments, the lipid bilayer incompatible surface comprises a lipophilic material. Any materials that tend to inhibit formation of a lipid bilayer may be used. A bubble of lipids filled with fast diffusing gas molecules is then formed on the lipid bilayer compatible surface. The bubble is herein termed a lipid bilayer initiating bubble. The gas molecules are allowed to diffuse out of the bubble and the bubble folds or collapses to form a lipid bilayer on the solid surface.

Various techniques may be used to form the lipid bilayer initiating bubble described above. For example, the lipid suspension deposited on the lipid bilayer compatible surface (e.g., electrode surface) may include chemicals that can react or decompose to form fast diffusing gas molecules. Fast diffusing gas molecules can be any gaseous molecules that can diffuse quickly through lipid layers. In general, larger molecules or ionic gaseous molecules do not diffuse very well through the lipid bilayer, while smaller nonpolar molecules can diffuse rapidly through the lipid bilayer. Examples of fast diffusing gaseous molecules include $O_2$ and $CO_2$. In one example, the lipid suspension includes potassium formate molecules and an bubble initiating electrical stimulus having a range of 0.3 V to 3.0 V is applied to the lipid suspension for 100 ms to 1 s to cause the formate molecules to decompose to form fast diffusing $C_2O$. In another example, a bubble initiating electrical stimulus having a range of 0.5 V to 3.0 V may be applied to a lipid suspension to oxidize $H_2O$ to form fast diffusing $O_2$ gas molecules.

The structural integrity and/or the electrical characteristics of the lipid bilayer may be examined using various techniques to make sure it has the necessary structural and/or electrical characteristics. In one example, an alternating current (AC) may be applied across the lipid bilayer to detect the capacitance of the lipid bilayer. In some embodiments, if the detected capacitance is greater than approximately 5 fF/$\mu m^2$, the lipid bilayer is considered to be properly formed and have the necessary structural and electrical characteristics, otherwise the lipid bilayer is not properly formed and an erasing electrical stimulus may be applied to erase the lipid bilayer so the process of assembling the lipid bilayer on the lipid bilayer compatible surface can be started all over again.

Furthermore, techniques for inserting a nanopore into a lipid bilayer are described herein. In one example, a solution containing nanopore forming molecules are deposited on the lipid bilayer, an agitation stimulus is applied across the lipid bilayer to disrupt the lipid bilayer and facilitate insertion of the nanopore into the lipid bilayer. The agitation stimulus may be any kind of stimulus that can cause disruption, preferably temporary disruption, of the lipid bilayer for facilitating nanopore insertion. It may be electrical, thermal, chemical, sound (audio), mechanical, and/or light stimuli. In one example, the agitation stimulus is an agitation electrical voltage level having a range of 100 mV to 1.0 V for 50 ms to 1 s.

In some embodiments, the lipid bilayer or the nanopore containing lipid bilayer is damaged or destroyed accidentally, or purposefully using a destruction electrical stimulus having a range of 300 mV to 3V (or −300 mV to −3 V) so that a new nanopore containing lipid bilayer can be formed over the planar solid surface. The destruction of the lipid bilayer may cause the surface underneath the lipid bilayer to oxidize or reduced. In such cases, a cleaning electrical stimulus having a magnitude of 50 mV to 300 mV may be applied to reverse the oxidation or reduction of the solid surface.

The lipid bilayer may be monitored to make sure that the desired number of nanopore(s) has been inserted and the lipid bilayer is not damaged during the process. In one example, a measuring electrical stimulus is applied across the lipid bilayer and a resistance (or ionic current) of the lipid bilayer is measured. The magnitude of the lipid bilayer resistance indicates whether any nanopore has been inserted into the lipid bilayer, if the nanopore has been inserted, how many nanopores have been inserted, and if the lipid bilayer has been damaged during the process. If it is determined that the desired number of nanopores has been inserted and the lipid bilayer has not been damaged during the process, the lipid bilayer may be used for characterizing molecules using the techniques described herein. If it is determined that no nanopore has been inserted, another agitation electrical stimulus may be applied. If it is determined that greater than the desired number of nanopores has been inserted or the lipid bilayer has been damaged, an erasing electrical stimulus may be applied across the lipid bilayer to erase the lipid bilayer in order to restart the process of creating lipid bilayer and inserting nanpore.

FIG. 1 is a schematic diagram of a nanopore device 100 that may be used to characterize a molecule as described in the examples described above where the nanopore containing lipid bilayer is characterized by a resistance and capacitance. The nanopore device 100 includes a lipid bilayer 102 formed on a lipid bilayer compatible surface 104 of a conductive solid substrate 106, where the lipid bilayer compatible surface 104 may be isolated by lipid bilayer incompatible surfaces 105 and the conductive solid substrate 106 may be electrically isolated by insulating materials 107, and where the lipid bilayer 102 may be surrounded by amorphous lipid 103 formed on the lipid bilayer incompatible surface 105. The lipid bilayer 102 is embedded with a single nanopore structure 108 having a nanopore 110 large enough for passing of at least a portion of the molecule 112 being characterized and/or small ions (e.g., $Na^+$, $K^+$, $Ca^{2+}$, $Cl^-$) between the two sides of the lipid bilayer 102. A layer of water molecules 114 may be adsorbed on the lipid bilayer compatible surface 104 and sandwiched between the lipid bilayer 102 and the lipid bilayer compatible surface 104. The aqueous film 114 adsorbed on the hydrophilic lipid bilayer compatible surface 104 may promote the ordering of lipid molecules and facilitate the formation of lipid bilayer on the lipid bilayer compatible surface 104. A sample chamber 116 containing a solution of the molecule 112 may be provided over the lipid bilayer 102 for introducing the molecule 112 for characterization. The solution may be an aqueous solution containing electrolytes and buffered to an optimum ion concentration and maintained at an optimum pH to keep the nanopore 110 open. The device includes a pair of electrodes 118 (including a negative node 118*a* and a positive node 118*b*) coupled to a variable voltage source 120 for providing electrical stimulus (e.g., voltage bias) across the lipid bilayer and for sensing electrical characteristics of the lipid bilayer (e.g., resistance, capacitance, and ionic current flow). The surface of the negative positive electrode 118*b* is or forms a part of the lipid bilayer compatible surface 104. The conductive solid substrate 106 may be coupled to or forms a part of one of the electrodes 118. The device 100 may also include an electrical circuit 122 for controlling electrical stimulation and for processing the signal detected. In some embodiments, the variable voltage source 120 is included as a part of the electrical circuit 122. The electrical circuitry 122 may include amplifier, integrator, noise filter, feedback control logic, and/or various other components. The electrical circuitry 122 may be integrated electrical circuitry integrated within a silicon substrate 128 and may be further coupled to a computer processor 124 coupled to a memory 126.

The lipid bilayer compatible surface 104 can be formed from various materials that are suitable for ion transduction and gas formation to facilitate lipid bilayer formation. In some embodiments, conductive or semi-conductive hydrophilic materials as opposed to insulating hydrophilic materials are preferred because they may allow better detection of a change in the lipid bilayer electrical characteristics. Example materials include Ag—AgCl, Ag—Au alloy, Ag—Pt alloy, or doped silicon or other semiconductor materials.

The lipid bilayer incompatible surface 105 can be formed from various materials that are not suitable for lipid bilayer formation and they are typically hydrophobic. In some embodiments, non-conductive hydrophobic materials are preferred, since it electrically insulates the lipid bilayer regions in addition to separate the lipid bilayer regions from each other. Example lipid bilayer incompatible materials include for example silicon nitride (e.g., $Si_3N_4$) and Teflon.

In one particular example, the nanopore device 100 of FIG. 1 is a alpha hemolysin (αHL) nanopore device having a single «HL protein 108 embedded in a diphytanoylphosphatidylcholine (DPhPC) lipid bilayer 102 formed over a lipid bilayer compatible silver-gold alloy surface 104 coated on a copper material 106. The lipid bilayer compatible silver-gold alloy surface 104 is isolated by lipid bilayer incompatible silicon nitride surfaces 105, and the copper material 106 is electrically insulated by silicon nitride materials 107. The copper 106 is coupled to electrical circuitry 122 that is integrated in a silicon substrate 128. A silver-silver chloride electrode placed on-chip or extending down from a cover plate 130 contacts an aqueous solution containing dsDNA molecules.

The αHL nanopore is an assembly of seven individual peptides. The entrance or vestible of the αHL nanopore is approximately 26 Å in diameter, which is wide enough to accommodate a portion of a dsDNA molecule. From the vestible, the αHL nanopore first widens and then narrows to a barrel having a diameter of approximately 15 Å, which is wide enough to allow a single ssDNA molecule to pass through but not wide enough to allow a dsDNA molecule to pass through. At a given time, approximately 1-20 DNA bases can occupy the barrel of the αHL nanopore.

In addition to DPhPC, the lipid bilayer of the nanopore device can be assembled from various other suitable amphiphilic materials, selected based on various considerations, such as the type of nanopore used, the type of molecule being characterized, and various physical, chemical and/or electrical characteristics of the lipid bilayer formed, such as stability and permeability, resistance, and capacitance of the lipid bilayer formed. Example amphiphilic materials include various phospholipids such as palmitoyl-oleoyl-phosphatidyl-choline (POPC) and dioleoyl-phosphatidyl-methylester (DOPME), diphytanoylphosphatidylcholine (DPhPC) dipalmitoylphosphatidylcholine (DPPC), phosphatidylcholine, phosphatidylethanolamine, phosphatidylserine, phosphatidic acid, phosphatidylinositol, phosphatidylglycerol, and sphingomyelin.

In addition to the αHL nanopore shown above, the nanopore may be of various other types of nanopores. Examples include γ-hemolysin, leukocidin, melittin, and various other naturally occurring, modified natural, and synthetic nanopores. A suitable nanopore may be selected based on various characteristics of the analyte molecule such as the size of the analyte molecule in relation to the pore size of the nanopore. For example, the αHL nanopore that has a restrictive pore size of approximately 15 Å. It is suitable for analyzing DNA molecules since it allows a single strand DNA (ssDNA) to pass through while restricting a double strand DNA (dsDNA).

Figure 2:
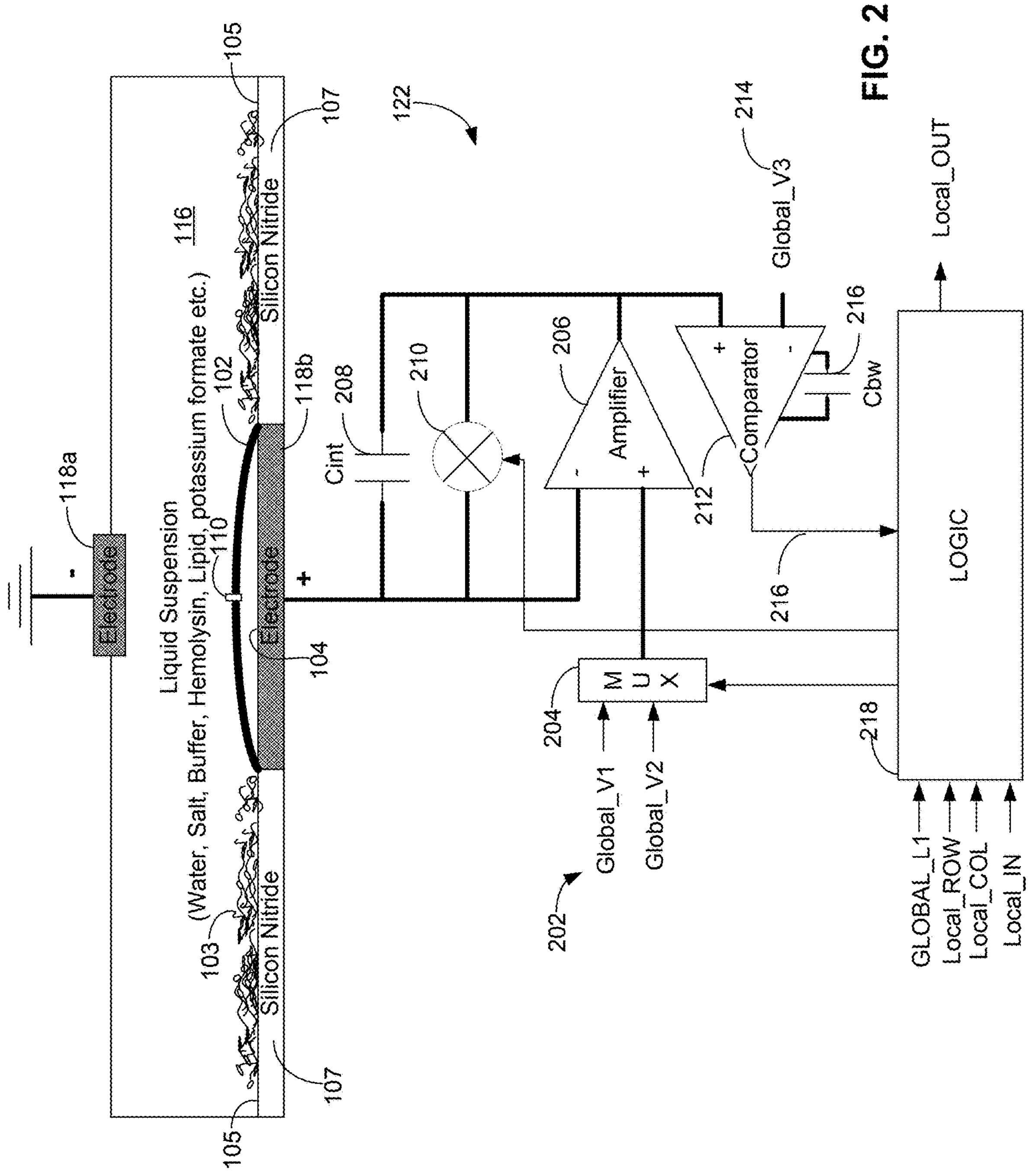
FIG. 2 is a schematic diagram of an embodiment of a circuit used in a nanopore device for controlling an electrical stimulus and for detecting electrical signatures of an analyte molecule.

FIG. 2 is a schematic diagram of an example electrical circuit 122 of a single cell of a nanopore array. The electrical circuit 122 is used for controlling the electrical stimulus applied across the lipid bilayer 102 which contains a nanopore and for detecting electrical signatures or electrical patterns of the molecule passing through the nanopore. The thick lines represent analog signal levels and the thin lines represent logic signal levels. As shown here, the circuit 122 includes a pair of electrodes 118*a*, 118*b* placed across the nanopore containing lipid bilayer 102. The surface of the positive electrode 118*b* forms the lipid bilayer compatible surface 104 and the surfaces of the adjacent silicon nitride 107 form the lipid bilayer incompatible surfaces 105. The input voltage applied across the lipid bilayer by the electrodes is controlled by selecting an input source from a plurality of input sources 202 at the multiplexer 204. Each of the plurality of voltage sources can provide DC, AC, pulse, ramp AC and/or ramp DC signals. The signal is amplified by an amplifier 206 and then compared with a set value 214 by a comparator 212, which outputs a signal when the amplified signal reaches the set value 214.

The time for the amplified signal to reach the set value 214 under a constant input voltage can be correlated with the resistance of the lipid bilayer and the ion current passing through the lipid bilayer. A longer time corresponds to a larger resistance and a smaller ion current through the lipid bilayer. The peak to peak amplitude of the amplified signal as detected by comparator 214 under a modulated input voltage (e.g., modulated with a sine wave) can be similarly correlated with the capacitance of the lipid bilayer. A larger peak to peak amplitude corresponds to a higher capacitance.

The circuit 122 further includes capacitor 216 for reducing noise levels and a switch 210 for resetting the capacitor 208. A logic controller 218 is provided to control the operation of the various components of the circuit and process the signal output of the comparator.

It should be noted that the above circuit design is only an example; other suitable circuit designs may also be used for controlling the electrical stimulus applied across the lipid bilayer and for measuring the electrical characteristics or signatures of the surface above the electrode, such as the electrical characteristics or signatures of the lipid suspension, lipid bilayer, nanopore containing lipid bilayer, and/or analyte molecule passing through the nanopore contained in the lipid bilayer.

Figure 3A:
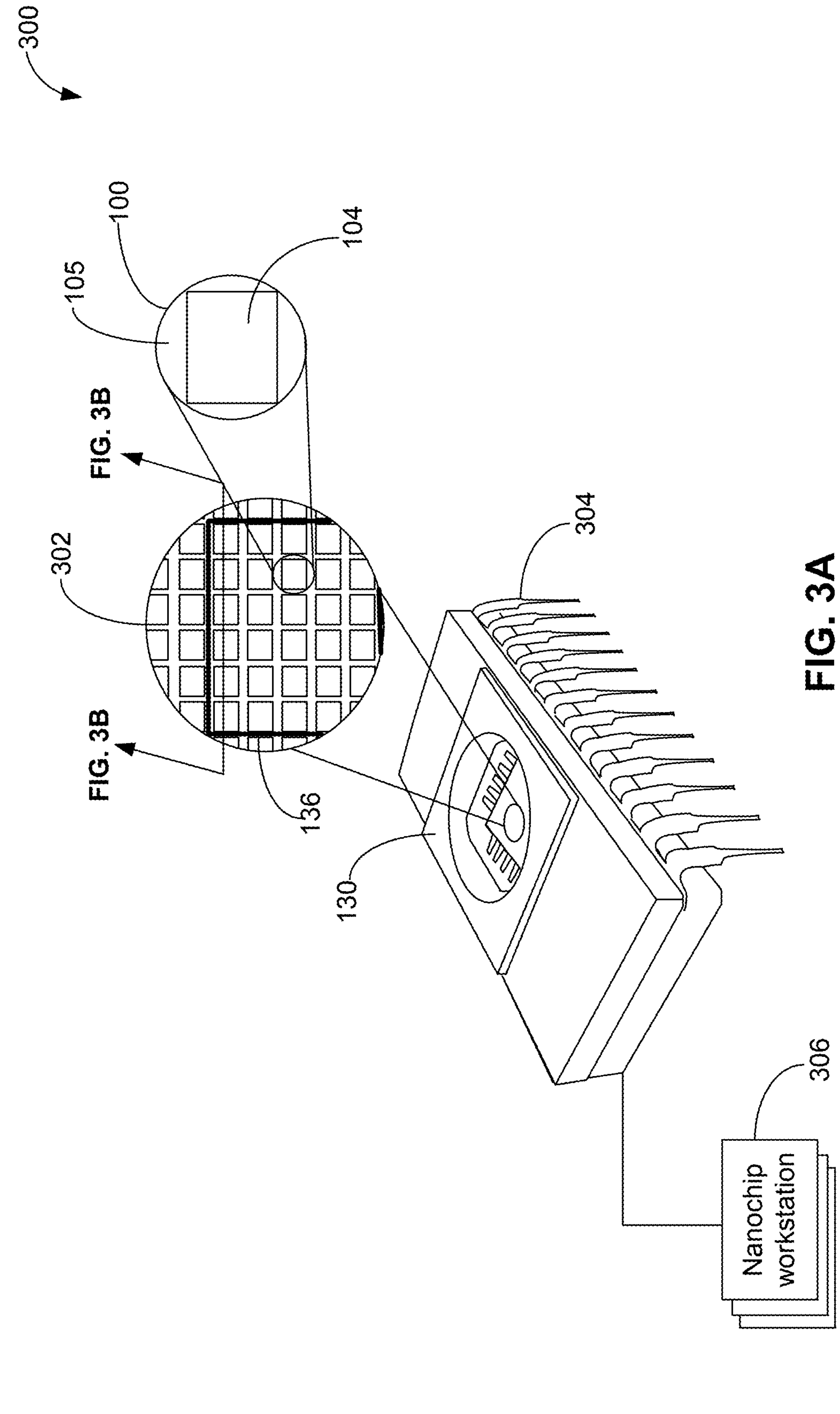
FIG. 3A is a perspective view of a schematic diagram of an embodiment of a chip that includes a nanopore device array.
Figure 3B:
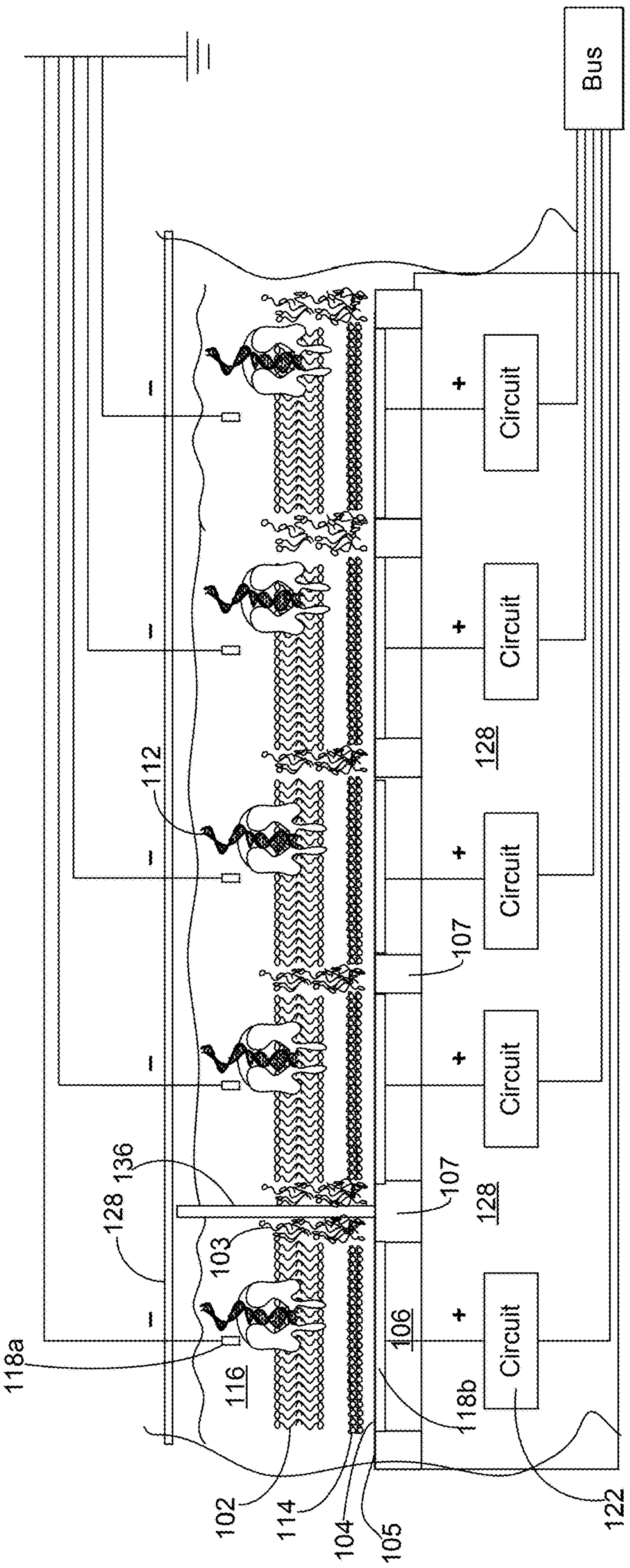
FIG. 3B is a cross sectional view of the chip shown in FIG. 3A.

FIG. 3A is a top view of a schematic diagram of an embodiment of a nanopore chip 300 having an array 302 of individually addressable nanopore devices 100 having a lipid bilayer compatible surface 104 isolated by lipid bilayer incompatible surfaces 105. Referring back to FIG. 1, each nanopore device 100 is complete with a control circuit 122 integrated on a silicon substrate 128. In some embodiments, side walls 136 may be included to separate groups of nanopore devices 100 so that each group may receive a different sample for characterization. With reference to FIG. 3A, in some embodiments, the nanopore chip 300 may include a cover plate 130. The nanopore chip 300 may also include a plurality of pins 304 for interfacing with a computer processor. In some embodiments, the nanopore chip 300 may be coupled to (e.g., docked to) a nanopore workstation 306, which may include various components for carrying out (e.g., automatically carrying out) the various embodiments of the processes of the present invention, including for example analyte delivery mechanisms such as pipettes for delivering lipid suspension, analyte solution and/or other liquids, suspension or solids, robotic arms, and computer processor, and memory. FIG. 3B is a cross sectional view of the nanopore chip 300.

Figure 4A:
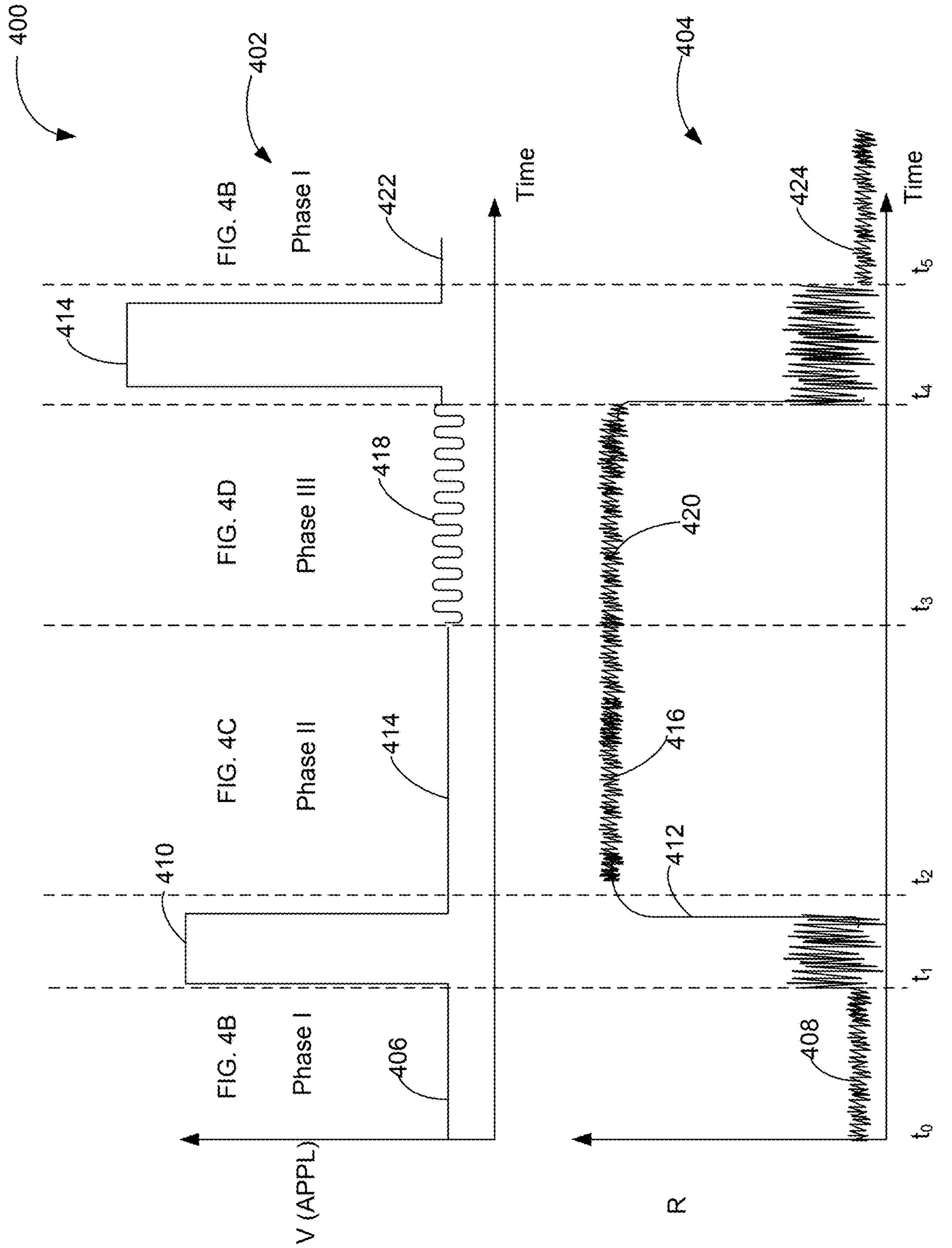
FIG. 4A is a schematic diagram depicting an embodiment of a process for forming a lipid bilayer on a solid substrate.
Figures 4B, 4C, 4D:
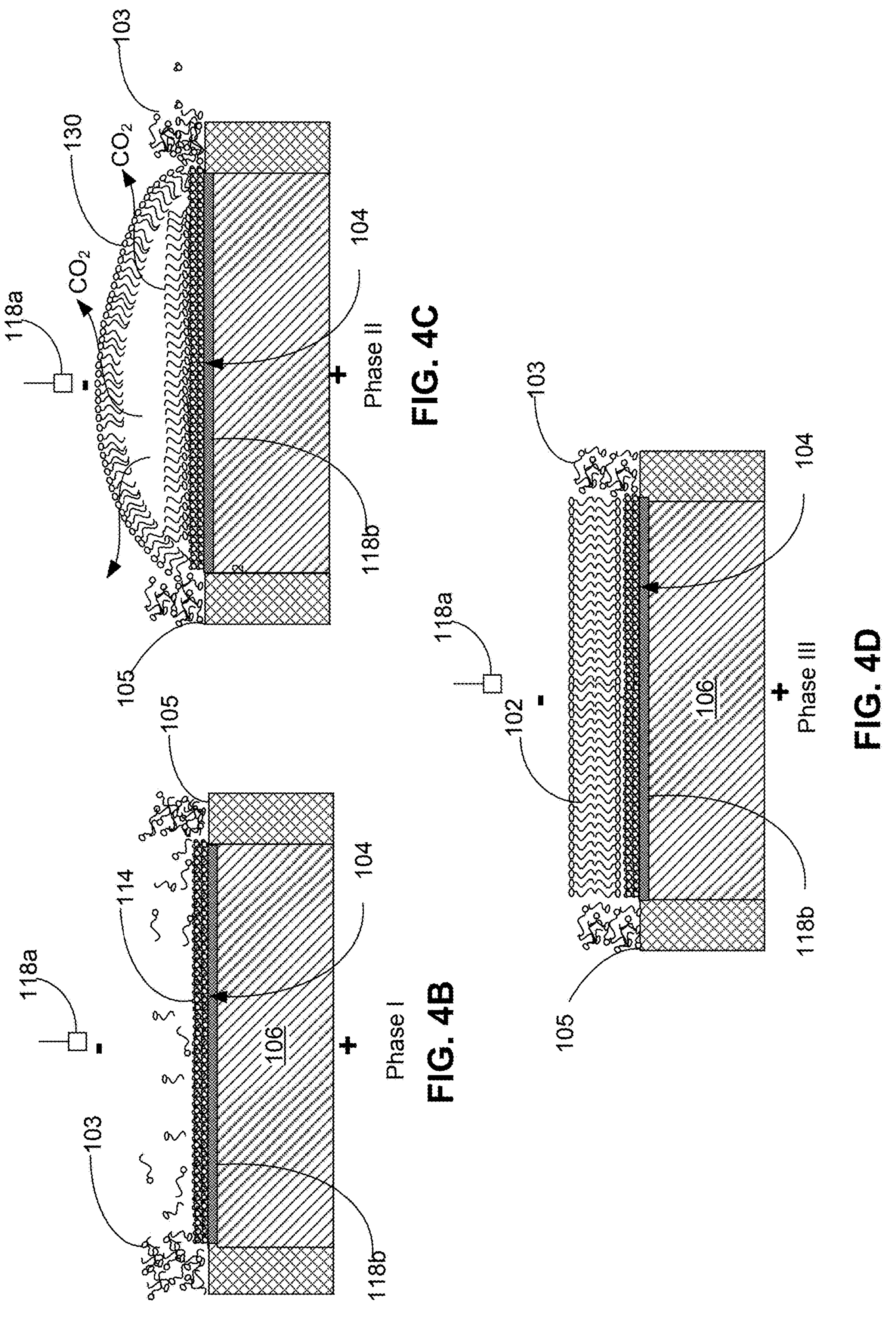
FIG. 4B illustrates phase I of the nanopore device 100 during process 400.
FIG. 4C illustrates phase II of the nanopore device 100 during process 400.
FIG. 4D illustrates phase III of the nanopore device 100 during process 400.

FIG. 4 is a schematic diagram depicting an example process 400A for assembling a lipid bilayer on the lipid bilayer compatible surface 104. The process 400A may be carried out using the nanopore device 100 of FIGS. 1 and 3. FIGS. 4B, 4C, and 4D illustrate the various phases of the nanopore device 100 during the process.

Referring back to FIG. 4A, in this example, the lipid bilayer is a diphytanoylphosphatidylcholine (DPhPC) lipid bilayer. The lipid bilayer compatible surface 104 is an Ag—Au alloy surface isolated by one or more lipid bilayer incompatible silicon nitride surfaces. One or more steps of the process may be automated using an electrical circuit, computer hardware and/or computer software. The top trace 402 represents the profile of a voltage applied across the lipid bilayer. The bottom trace 404 represents a resistance profile detected across the lipid bilayer.

At time to, an aqueous lipid suspension containing 10 mg/mL colloidal diphytanoylphosphatidylcholine (DPhPC) dissolved in decane and 0.1 M potassium formate dissolved in 1 M KCl is deposited on the Ag—Au alloy electrode surface. The lipid suspension may be deposited for example using a liquid dispenser such as a pipette. In some embodiments, the liquid dispenser may be automated with various hardware (e.g., robotic arms) and software. Ag—Au alloy is hydrophilic and causes the lipid molecules to self-organize on its surface in a way that promotes lipid bilayer formation.

At time $t_0$-$t_1$, the nanopore device is in Phase I (illustrated in FIG. 4B). In Phase I, amorphous lipids 103 concentrate on the lipid bilayer incompatible surface 105 and are only barely present over the lipid bilayer compatible surface 104. A measuring voltage (~50 mV) 406 is applied to the electrode. The resistance versus time profile 408 of the electrode shows that the resistance is relatively low (~10 KΩ to 10 MΩ) and the electrode is shorted.

At time $t_1$, a bubble initiating stimulus 410 having a range of ~1.4 V to ~3.0 V and a duration of ~100 ms to ~1 s is applied across the electrode. The bubble initiating stimulus 410 causes the formate, which we believe is mostly present over the hydrophilic lipid bilayer compatible silver-gold alloy surface and not over the hydrophobic lipid bilayer incompatible silicon nitride surface, to decompose to form gaseous $CO_2$, which causes a bubble 130 to form on the solid silver-gold alloy electrode surface. The nanopore device is in Phase II (illustrated in FIG. 4C). The bubble covers the electrode and stops when it reaches the amorphous lipid material 103 at the edge of the lipid bilayer compatible surface 104. An electrical and mechanical seal is formed over the lipid bilayer compatible surface. The resistance versus time profile 412 at time $t_1$-$t_2$ shows a dramatic increase in resistance (e.g., >10 GΩ) due to the formation of the bubble.

At time $t_2$-$t_3$ (~100 ms to 1 s), $CO_2$ diffuses out of the bubble rapidly, causing the bubble to collapse and gradually form a lipid bilayer. The nanopore device is in Phase II (illustrated in FIG. 4C) 102 over the solid electrode surface 104. The lipid bilayer is surrounded by amorphous lipid 103 aggregated over the lipid bilayer incompatible silicon nitride surface 105. The resistance across the nanopore device 416 under an applied measuring voltage (~50 mV) 414 remains high due the presence of the lipid bilayer 102.

At time $t_3$-$t_4$ (~50 ms to 500 ms), a lipid bilayer 102 has been formed and the nanopore device is in Phase III (illustrated in FIG. 4D). An alternating current 418 is applied across the lipid bilayer to check for proper lipid bilayer resistance 420 and/or capacitance (not shown). A properly formed lipid bilayer with sound structural integrity is determined to be formed if the measured capacitance has a value greater than approximately a 5 fF/$\mu m^2$ and if the measured resistance has a value greater than approximately 10 GΩ. Otherwise, the lipid bilayer is determined to have poor structural integrity. If it is determined that the lipid bilayer has sound structural integrity, the nanopore device 100 is ready for nanopore insertion as will be illustrated in reference to FIG. 5. If it is determined that the lipid bilayer has poor structural integrity, a destruction or erasing electrical stimulus (e.g., ~2 V) is applied across the lipid bilayer to erase the lipid bilayer. The nanopore device 100 reverts back to Phase I (illustrated in FIG. 4B).

Figure 5A:
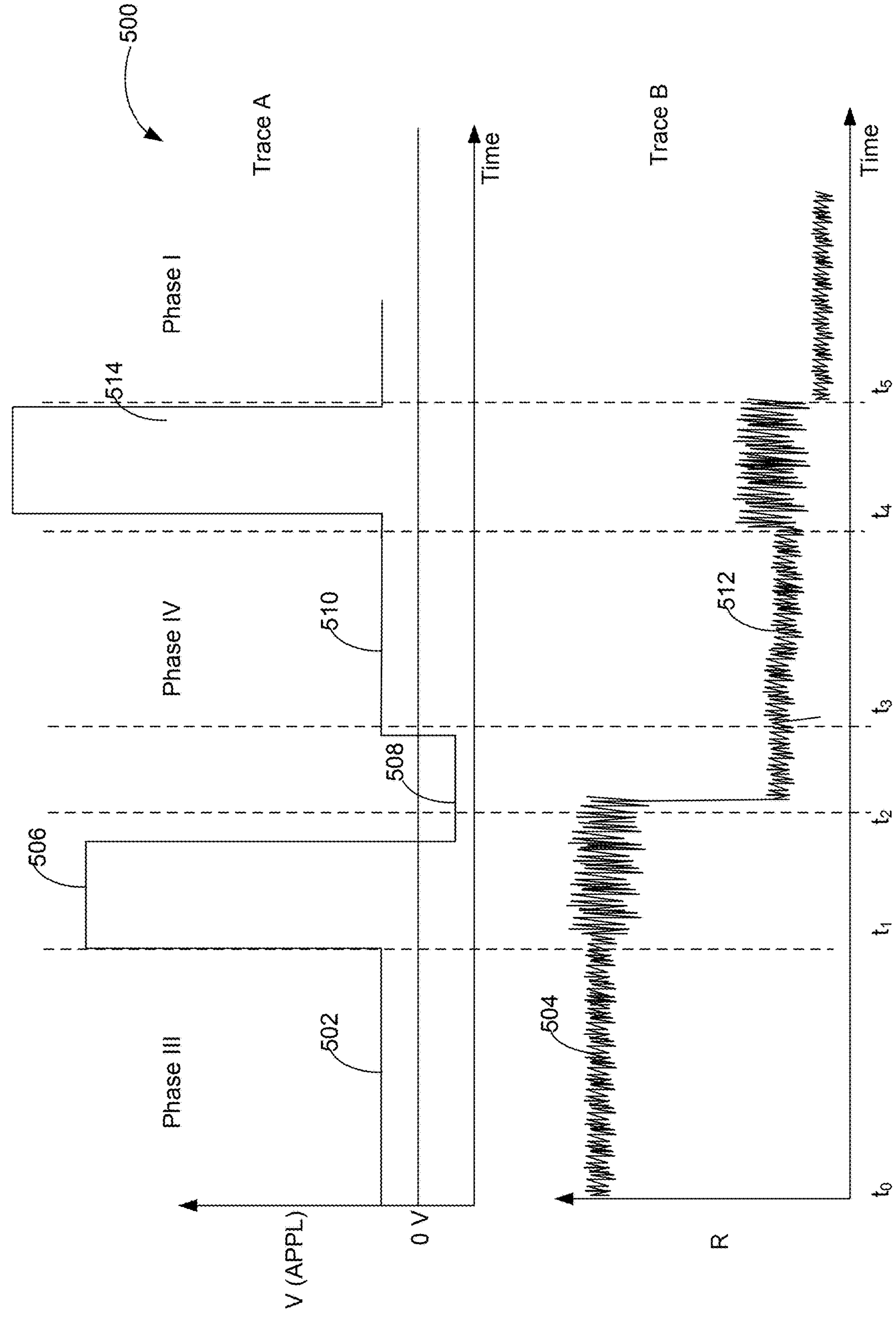
FIG. 5A is a schematic diagram of an embodiment of a process for inserting a nanopore into a lipid bilayer.

FIG. 5A is a schematic diagram of an embodiment of a process 500 for inserting a nanopore into a lipid bilayer. The process may be implemented using the nanopore device 100 of FIG. 1 or 3. The one or more steps of the process may be automated using hardware (e.g., integrated circuit) and/or computer code. The bilayer forming process is monitored using the nanopore device 100 of FIG. 1. Trace A represents a voltage applied across the lipid bilayer. Trace B represents the resistance detected across the lipid bilayer. FIGS. 5B-E illustrate various phases the nanopore device 100 is in during the process.

Figures 5B, 5C, 5D, 5E:
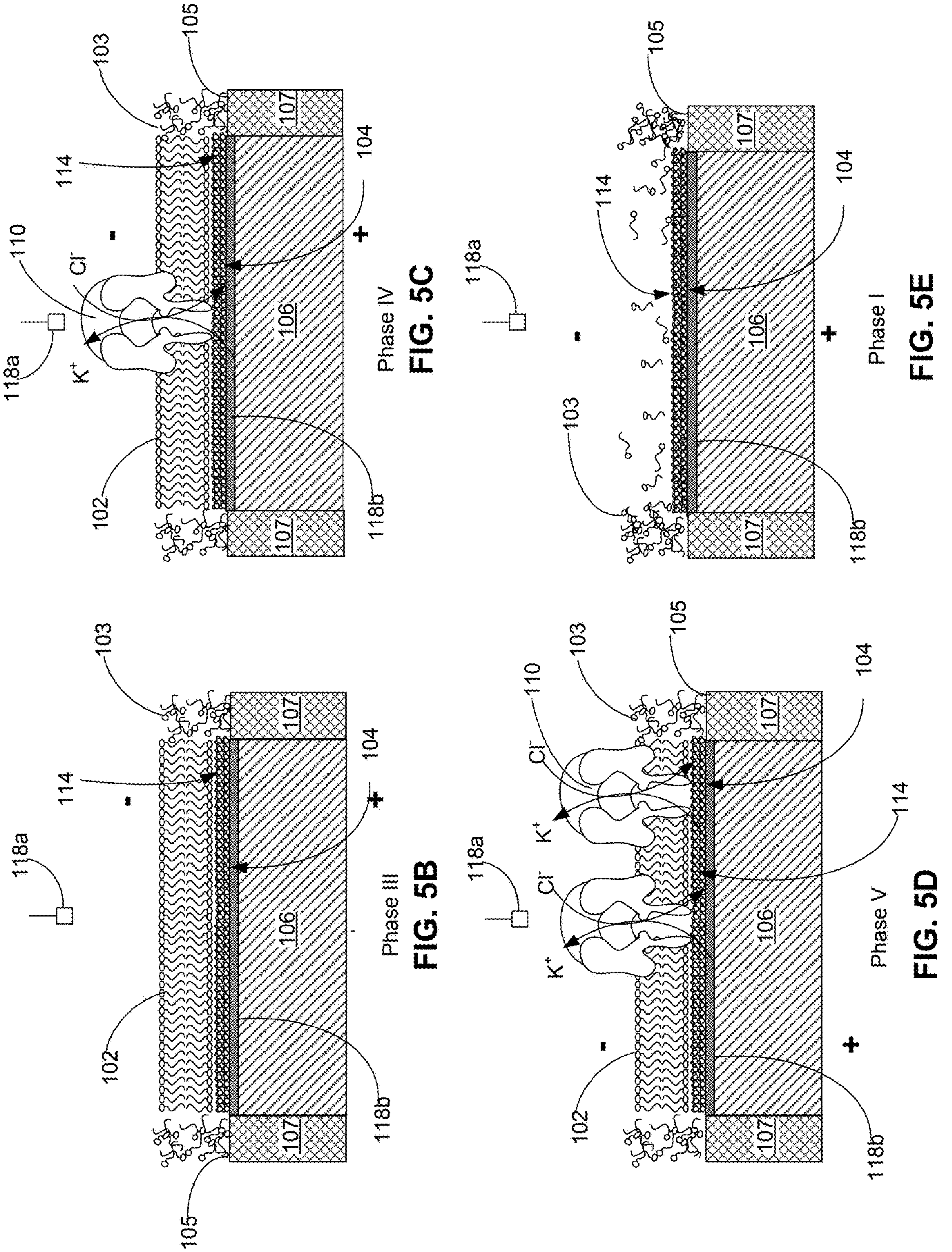
FIG. 5B illustrates phase III of the nanopore device 100 during process 500.
FIG. 5C illustrates phase IV of the nanopore device 100 during process 500.
FIG. 5D illustrates phase V of the nanopore device 100 during process 500.
FIG. 5E illustrates phase I of the nanopore device 100 during process 500.

Referring back to FIG. 5A, at time $t_0$-$t_1$, the nanopore device includes a structurally sound lipid bilayer membrane and the nanopore device is in Phase III (illustrated in FIG. 5B). A solution containing α-hemolysin, a nanopore forming peptides, is over the lipid bilayer. Applying a measuring stimulus (e.g., ~50 mV) 502 across the lipid bilayer returns a resistance value 504 that falls in the desired range (~10 GΩ), indicating a lack of ionic current through the lipid bilayer.

At time $t_1$-$t_2$, an agitation electrical stimulus 506 (~100 mV to 1.0 V for 50 ms to 1 s) is applied across the lipid bilayer membrane, causing a disruption in the lipid bilayer and initiating the insertion of α-hemolysin nanopore into the lipid bilayer.

At time $t_2$-$t_3$ and immediately following the agitation electrical stimulus 506, a negative electrical stimulus 508 is applied. The negative pulse is intended to reverse any oxidation (e.g., oxidation of the electrodes) that may have been caused by accidental bursting of the lipid bilayer.

At time $t_3$-$t_4$, a measuring electrical stimulus (~50 mV) 510 is applied to check for proper nanopore insertion. The magnitude of the measured resistance 512 gives an indication whether the nanopore has been inserted, and if nanopore is inserted how many nanopores have been inserted, and whether the lipid bilayer has been disrupted or destroyed during the process. 512 shows an example of a drop in resistance with the insertion of a nanopore. For example, a lipid bilayer with no nanopore inserted would have a resistance in the range of 10 GΩ, a lipid bilayer with a single nanopore inserted (Phase IV, illustrated in FIG. 5C) would have a resistance in the range of 1 GΩ, a lipid bilayer with two or more nanopores inserted (Phase V illustrated in FIG. 5D) would have a resistance in the range of ~500 MΩ, and a disrupted or damaged lipid bilayer would have a resistance in the range of less than approximately 10 MΩ. If it is determined that no nanopore has been inserted in the lipid bilayer, another agitation electrical stimulus may be applied. If it is indicated that a single nanopore has been inserted and the lipid bilayer is structurally sound, the process stops and the nanopore device is ready for analyzing the analyte molecule. If it is detected that more than one nanopore has been inserted or the lipid bilayer is disrupted, an erasing or destruction electrical stimulus (~300 mV to 3 V) 514 can be applied to erase the lipid bilayer. The lipid bilayer electrode is once again shorted and the nanopore device is in (Phase I, illustrated in FIG. 5E). The destruction electrical stimulus can be followed by a cleaning electrical stimulus (50 mV to 300 mV) to reverse the oxidation that may have occurred on the electrode surface due to the destruction of the lipid bilayer. The whole process of assembling lipid bilayer (e.g., FIG. 4) and inserting nanopore (e.g., FIG. 5) can be started over again.

In other techniques, nanopores are self-assembled. In these techniques, the concentration of the nanopore forming solution must be high enough such that the nanopores are inserted into the lipid bilayers automatically and without any external stimulus. Such self-assembly techniques have a number of drawbacks. For example, if the concentration of the nanopore forming solution is too low, then no nanopores are inserted into the lipid bilayers. If the concentration is too high, then multiple nanopores may be formed in a lipid bilayer, unless the nanopore forming solution is flushed after the first nanopore is formed. In addition, there is little or no control of when the nanopores will be formed.

In contrast to the self-assembly techniques, the present application discloses an electroporation technique in which an agitation electrical stimulus 506 is applied across the lipid bilayer membrane to disrupt the lipid bilayer and initiate the formation of a nanopore in the lipid bilayer. The concentration of the nanopore forming solution may be readily maintained at a sufficiently low enough level such that no nanopores are inserted automatically into the lipid bilayers. In addition, the agitation electrical stimulus 506 may be applied in such a way that only a single nanopore is inserted into each lipid bilayer.

Electroporation allows lower amounts (lower concentration) of hemolysin protein in the nanopore forming solution to achieve pore insertions. In some embodiments, the concentration of pore protein is at a level such that when applied to an array of bilayer-covered sensors, less than 10 percent of the bilayers have pores inserted in an uncontrolled manner. Using a lower concentration of pore protein has a number of advantages. For example, a user can have better control of the pore insertion because once a pore is inserted by electroporation, a second pore is unlikely to be inserted by itself. Using a lower concentration of pore protein is more economical. In addition, a lower concentration of pore protein is safer for the user to handle. For example, a high concentration of pore protein spilled on human skin may cause a severe rash, thus posing a health hazard.

If the electroporation technique described herein is not used, but a solution of protein pores is simply applied to an array of independent bilayers, it is well known to those skilled in the art that the insertion of protein pores into lipid bilayers will follow a Poisson distribution. This independent, randomness in pore insertion over time means that not only pore insertions are uncontrolled but that insertions are independent of prior events and therefore illustrates that more than one pore can be inserted into a single bilayer. Such a random system limits the percentage of single pore instances that one may obtain using concentration of pore protein alone. Changing a nanopore system from a random set of events with a Poisson distribution to a system with active, deterministic pore insertion (not following the Poisson distribution) gives the new system great advantage in attaining a higher percentage of bilayers with single pores.

The level of the agitation electrical stimulus 506 at which a nanopore is inserted into a lipid bilayer may vary based on various factors, including salt concentration, temperature, the type of lipid membrane material, size of the lipid bilayer, and the like. In some embodiments, about 80-90% of the nanopores are inserted when the magnitude of the agitation electrical stimulus 506 is within the range of 200 mV to 450 mV. The rest of the nanopores may be inserted at lower voltage levels, e.g., 100 mV or at higher levels, e.g., 700 mV.

In some embodiments, the steps of applying the agitation electrical stimulus 506, applying the negative stimulus (reverse oxidation stimulus) 508, and applying the measuring electrical stimulus 510 for detecting whether a nanopore has been properly formed are iterated in a loop, until a nanopore is finally formed in the lipid bilayer. Initially, the magnitude of the agitation electrical stimulus 506 is set at a lower level. The magnitude of the agitation electrical stimulus 506 is then gradually increased after each iteration. For example, the initial agitation electrical stimulus 506 may be set at a lower level, such as 60 mV. After each iteration, if a nanopore is still not properly inserted, then the agitation electrical stimulus 506 is adjusted by a small increment, e.g., 2 mV. This process may be repeated until a nanopore is finally inserted into the lipid bilayer, or until the lipid bilayer is damaged or erased by the agitation electrical stimulus 506, or until the agitation electrical stimulus 506 has reached a predetermined maximum threshold, e.g., 700 mV. By gradually increasing the agitation electrical stimulus 506 level (e.g., from 60 mV to 700 mV) as describe above, a higher percentage of the cells of the nanopore chip will have one nanopore properly inserted into a lipid bilayer.

In FIG. 5A, agitation electrical stimulus 506 is shown as a positive voltage. However, a negative agitation electrical stimulus may be used in some embodiments as well. When a negative agitation electrical stimulus is used, a positive pulse may be used to reverse any oxidation (e.g., oxidation of the electrodes).

Because individual pore protein mixes can have smaller or larger percentages of well-formed, active pore molecules, the desired concentration to use for different batches of pore protein varies. In some embodiments, a particular pore protein mix is first tried on a chip to see how active it is and then the concentration is adjusted until application of the mix will put only a few (e.g., 0-10) pores into an array of 264 bilayer covered electrodes without any stimulation. In general, a concentration may be chosen that results in less than about 10 percent pore formation un-stimulated. In some embodiments, a concentration may be chosen that results in less than about 30 percent pore formation un-stimulated. At such a concentration level, an insignificant number of pores will be inserted when the mix is simply left on the array with no stimulation. At this low concentration, electroporation techniques will insert pores between −100 mV and −600 mV. Positive pulses can be used as well.

In some embodiments, applying concentrations of alpha-hemolysin or MspA pores in the range of 0.1 ng/ml (nanogram) to 2 μg/mL (microgram) of pore protein will typically result in the preferred condition of having only a few pores inserted in a field of 264 bilayer covered electrodes unaided. The exact concentration used may be determined after calibration on a chip and prior to distribution of the protein pore mix to researchers. In such a case, the resulting protein mix is diluted to the optimal level and then stored for future use and distribution to researchers where further calibration is not necessary.

The amount or concentration needed to reach the desired state described above varies with salt concentration, temperature, pressure, and the dimensions of the bilayers covering the electrodes. Higher temperatures or pressures require lower pore concentration. Larger bilayer diameters also require a lower pore concentration to successfully implement an electroporation scheme for directed, controlled pore insertion. The pore concentrations above take into account possible variations for salt concentrations (KCl or NaCl) (e.g., from 50 mM to 1M), temperatures (e.g., from 0 degree Celsius to 25 degree Celsius), pressures (e.g., normal barometric pressure at sea level), and bilayer diameters (e.g., from approximately 5 μm to 250 μm). The technique described above of testing a given mix or representative mix allows for these variances to be taken into account.

Figure 6A:
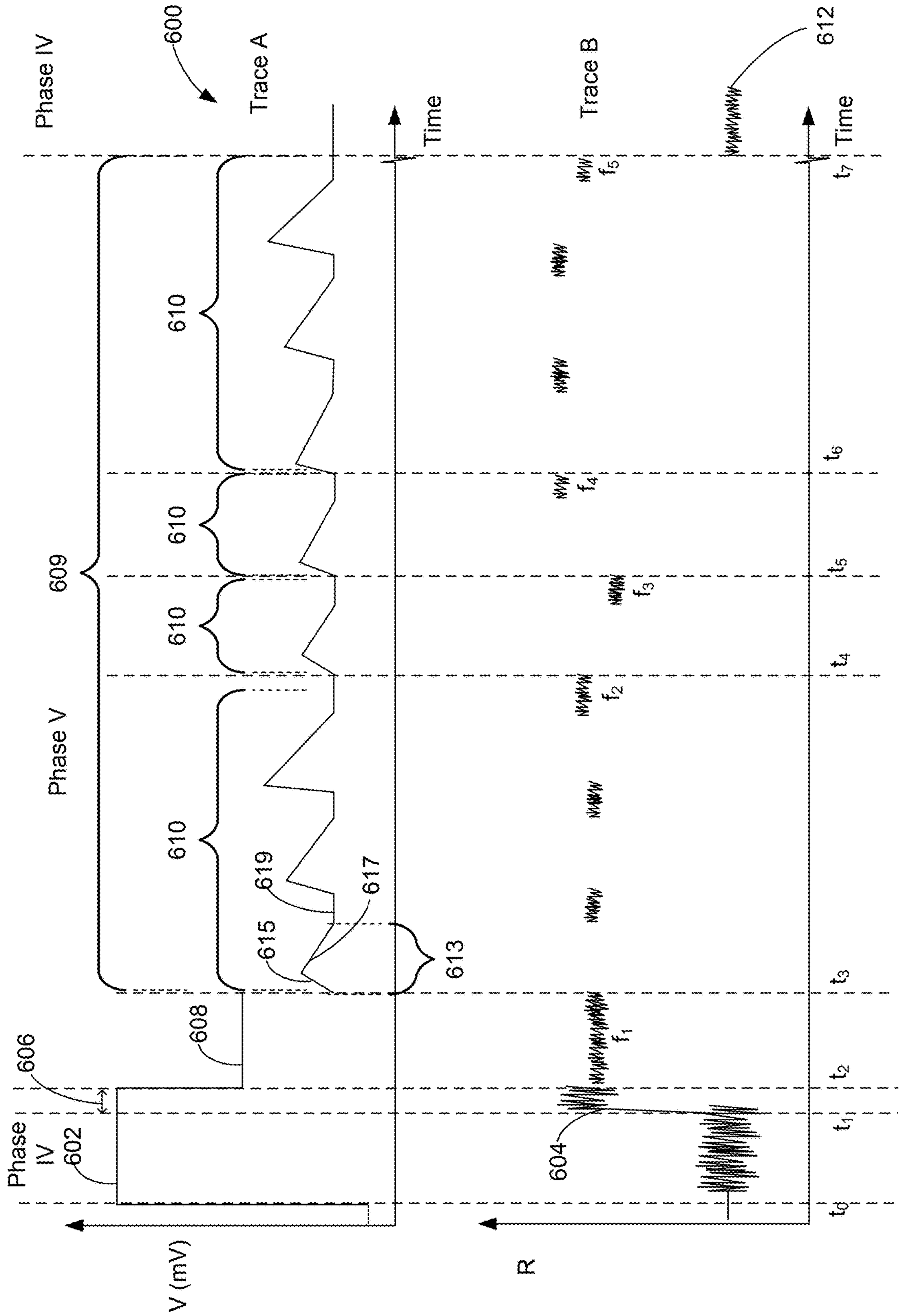
FIG. 6A is a schematic diagram illustrating an embodiment of a process for manipulating, detecting, characterizing, correlating, analyzing and/or sequencing a molecule in a nanopore.
Figure 6C:
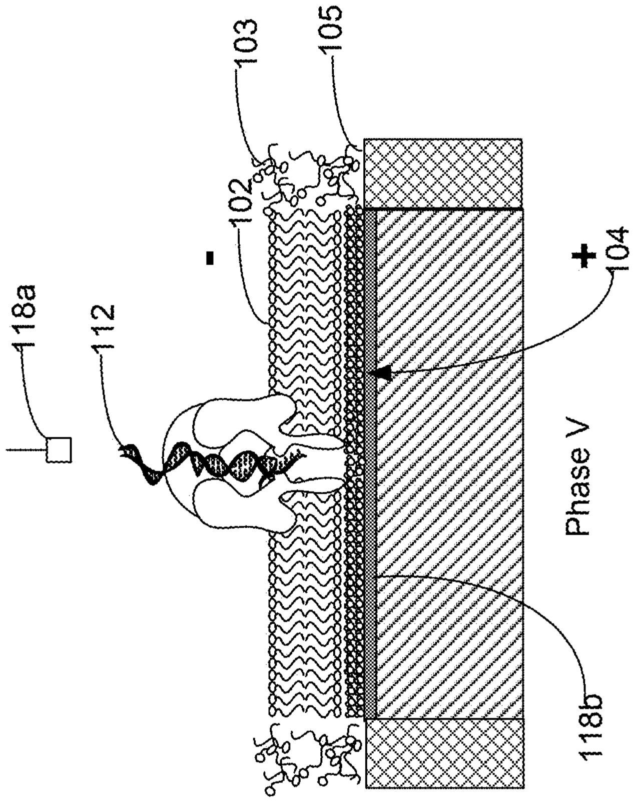
FIG. 6C illustrates phase V of the nanopore device during process 600.
Figure 6B:
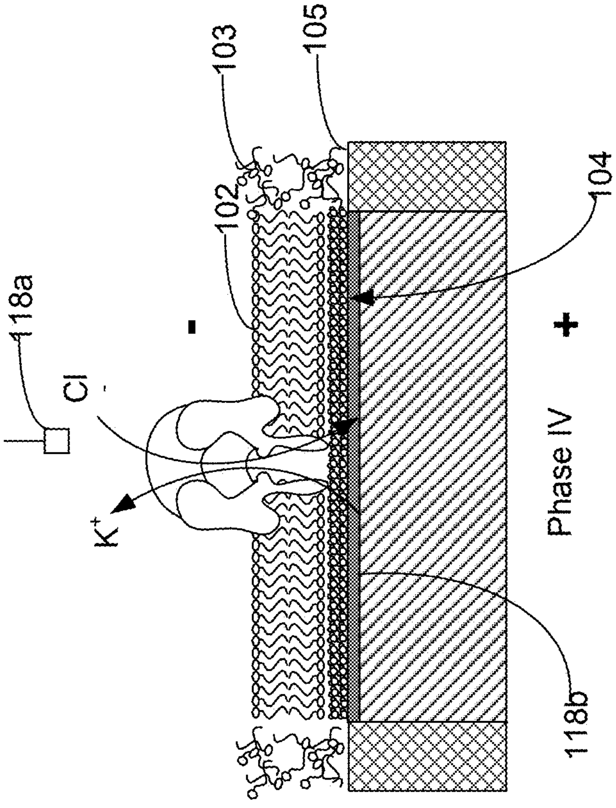
FIG. 6B illustrates phase IV of the nanopore device during process 600.

FIG. 6A is a schematic diagram illustrating an embodiment of a process 600 for manipulating, detecting, correlating, characterizing, analyzing and/or sequencing a molecule in a nanopore using a nanopore device. One or more steps of the process may be automated via hardware (e.g., integrated circuit) and/or execution of a computer code. In the example illustrated, a dsDNA molecule is characterized using a αHL nanopore inserted in a lipid bilayer such as a DPhPC lipid bilayer formed on the nanopore device as illustrated in FIG. 1 or 3. FIGS. 6B-C illustrate the various phases the nanopore device is in during the process.

Referring back to FIG. 6A, Trace A represents a voltage applied across the nanopore containing lipid bilayer. Trace B represents the resistance detected across the nanopore containing lipid bilayer. At time to, an analyte solution containing a double stranded DNA (dsDNA) molecule is presented to the lipid bilayer, by for example depositing the analyte solution adjacent to the lipid bilayer. The analyte solution in this example is an aqueous solution containing the analyte molecule and small electrolytes (e.g., $Na^+$, $K^+$, $Ca^{2+}$, $Cl^-$) that is buffered to an appropriate pH 7.5 to 8.0. The nanopore has an open channel and the resistance of the nanopore containing lipid bilayer has a resistance of approximately 1GΩ (Phase IV, illustrated in FIG. 6A)

At time $t_0$-$t_1$, an acquiring electrical stimulus (~100 mV to 400 mV) 602 is applied across the lipid bilayer of the nanopore device, causing a single dsDNA molecule to be captured in the nanopore (Phase V, illustrated in FIG. 6A). The resistance versus time profile shows a sharp increase in resistance 604 to 6 GΩ which corresponds to an obstructed pore state (Phase V, illustrated in FIG. 6C) where the nanopore is partially blocked by a dsDNA molecule.

At time $t_1$-$t_2$, the sharp increase in resistance 604 triggers a control mechanism (e.g., the feedback control mechanism in circuit 122 of FIG. 2) to lower the electrical stimulus to a holding electrical stimulus (~50 mV to 150 mV) 608 with a fast response time (e.g., <10 mS) 606 in order to hold the dsDNA in the nanopore for detection, characterization and/or analysis. The short response time allows the analyte molecule to be trapped in the nanopore for characterization rather than passing through the nanopore and exiting through the other end.

At time $t_2$-$t_3$, the dsDNA molecule is held in the nanopore with the holding electrical stimulus, a first frame ($f_1$) of resistance versus time profile is recorded.

Subsequently from $t_3$-$t_7$, multiple series of variable progression electrical stimuli 609 are applied to the DNA molecule trapped in the nanopore, where each series of the variable progression electrical stimuli 610 comprises successively higher or more intense electrical pulses 613. As illustrated, each of the electrical pulses 613 comprises a ramp-up phase 615, a ramp-down phase 617, resembling a reversed "V" and having a range of approximately 100 mV to 200 mV. Each of the electrical pulses 613 is followed by a hold phase 619. As illustrated, the slope of the initial ramp-up phase 615 is steeper than the slope of the subsequent ramp-down phase 617. Each series of electrical pulses 610 may result in a frame (e.g., 1 to 20 base pairs) of the dsDNA molecule to be unzipped and the single strand of the unzipped dsDNA frame pulled through the nanopore under the applied progression electrical stimulus. The electrical pattern or signature of the frame of molecule is measured during each of the hold phases 619. The details are as follows:

At time $t_3$-$t_4$, a series of successively higher progression electrical stimulus (e.g., asymmetric electrical pulses) 610 is applied across the lipid bilayer to drive the dsDNA through the nanopore. After each electrical pulse 613, the resistance versus time profile is monitored during the hold phase 619 immediately following the electrical pulse 613. If the resistance versus time profile detected is the same as that of the previous frame $f_1$, it indicates that the electrical stimulus level is not high enough to drive the DNA molecule through the nanopore, and a higher electrical stimulus level is applied. The process of successively applying a higher electrical stimulus level is repeated until a different resistance versus time profile indicates that a new frame $f_2$ has been obtained and the new frame is recorded.

At time $t_4$-$t_5$, the previous process of applying successively higher progression electrical stimulus to pull the DNA molecule is repeated until a new frame $f_3$ is obtained.

At time $t_5$-$t_6$, the previous process of applying variable and successively higher progression electrical stimulus to pull the DNA molecule is repeated to obtain a new frame $f_4$ is recorded.

At time $t_0$-$t_7$, the previous process of applying successively higher progression electrical stimulus is repeated to obtain a new frame $f_5$. This process of applying successively higher progression electrical stimulus to obtain a new frame may be repeated.

At time beyond $t_7$, the resistance versus time profile may reach a level that corresponds to an open state for the nanopore (Phase IV, illustrated in FIG. 6B) 612. This indicates that the DNA molecule has escaped the nanopore and the flow of ions in the nanopore is unhindered by DNA molecule.

Each of the various frames ($f_1$ to $f_5$) corresponds to a resistance information when a particular region of the DNA molecule is lodged in the narrow passage of the nanopore. The various frames, separately or in combination, can be used to elucidate, detect, correlate, determine, characterize, sequence and/or discriminate various structural and chemical features of the analyte molecule as it traverses the nanopore. In some embodiments, one or more frames of the molecule may overlap. The overlapping of the sampling frames may allow for a more accurate characterization of the DNA molecule. For example, a single strand of a dsDNA molecule is threaded through the nanopore and the ssDNA has a sequence of 5'TGACTCATTAGCGAGG . . . 3'. The first frame of the molecule is the electrical signature detected for the segment TGACT, the second frame is the electrical signature detected for ACTCA, the third frame is the electrical signature detected for TCATT, and the fourth frame is the electrical signature detected for ATTAG, and so on and so forth. The electrical signatures of the various overlapping frames can be combined and deconvolved to generate a more accurate electrical signature of the molecule.

Figures 7A, 7B, 7C, 7D:
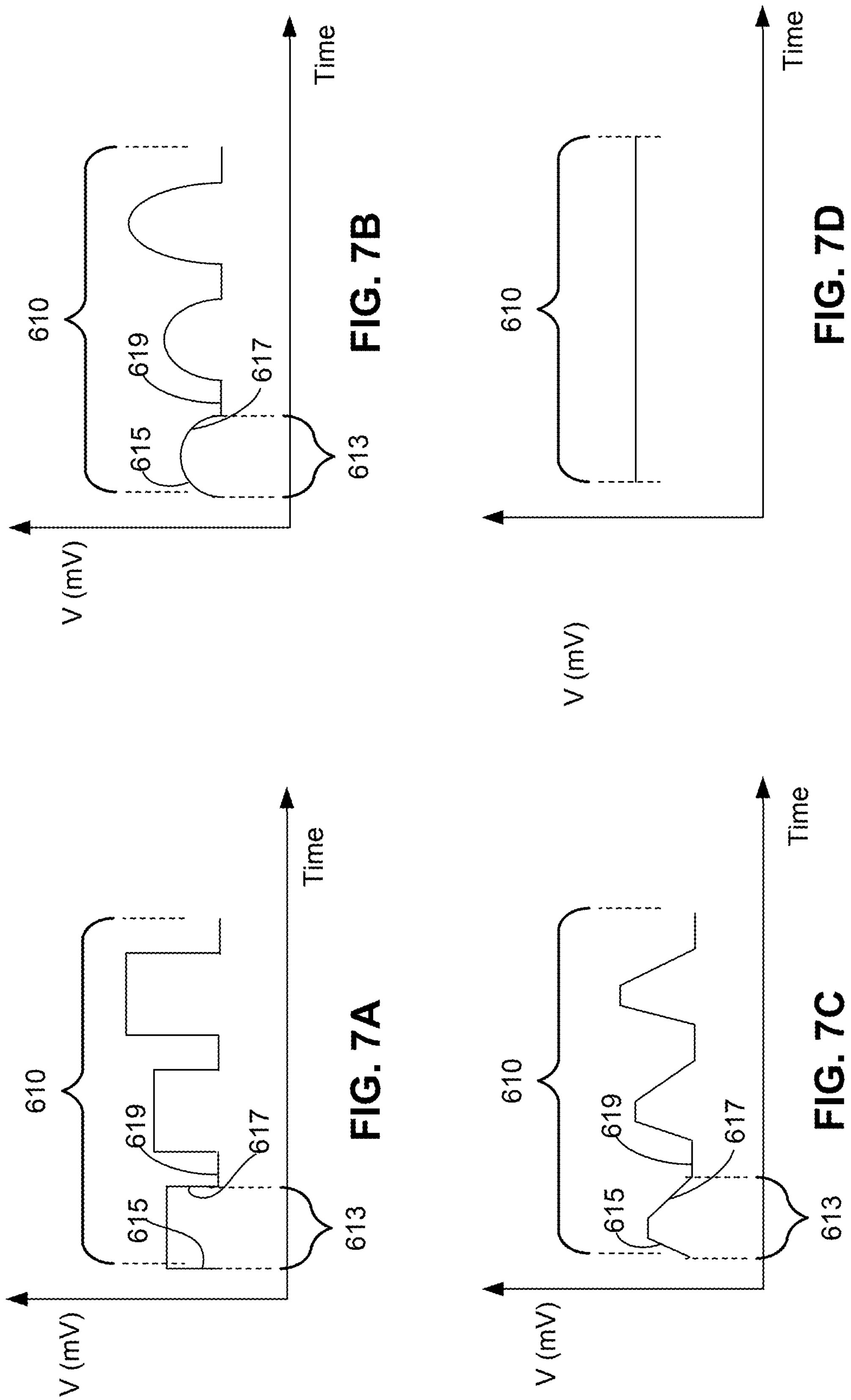
FIG. 7A illustrates an embodiment of a progression electrical stimulus.
FIG. 7B illustrates an embodiment of a progression electrical stimulus.
FIG. 7C illustrates an embodiment of a progression electrical stimulus.
FIG. 7D illustrates an embodiment of a progression electrical stimulus.

Although in this example, reversed "V" shaped progression electrical stimuli pulses 613 with an initial ramp-up phase 615 and a subsequent ramp-down phase 617 are used, other types of the progression electrical stimuli pulses may be used. In some embodiments, the progression electrical stimuli pulses may resemble a square wave (as illustrated in FIG. 7A), a smooth wave (as illustrated in FIG. 7B), or a reversed "U" with a flat center (as illustrated in FIG. 7C). In some embodiments, the progression electrical stimulus does not have the ramp-up phase 615 and the ramp-down phase 617, for example the progression electrical stimulus includes a steady constant progression electrical stimulus 610 (as illustrated in FIG. 7D).

Although in this example, a hold phase 619 follows each of the progression electrical stimuli pulses 613 and the electrical signature of the molecule is measured during the each of the hold phases 619, in other embodiments the hold phases 619 may be eliminated and the electrical signature of the molecule may be measured (e.g., continuously) while the progression electrical stimuli are applied and while the molecule is moving through the nanopore under the applied progression electrical stimuli. In one example, reversed "V" shaped progression electrical stimuli pulses 613 are applied without the hold phases 619, the electrical signature of the molecule is measured as the progression electrical stimulus is ramped up and ramped down (e.g., applied voltage at the electrode is ramping up or down). In such instances, the electrical signature of the molecule (e.g., resistance profile of the molecule) can be determined as a function of varying progression electrical stimulus level (e.g., varying voltage level) and such information can be used to differentiate different molecules (e.g., different DNA frames) being characterized. In another example, a constant progression electrical stimulus is applied without a hold phase and the electrical signature of the molecule is measured as the constant progression electrical stimulus is applied and while the molecule is moving through the nanopore under the constant progression electrical stimulus.

As discussed previously FIGS. 7A-D illustrate various embodiments of the progression electrical stimulus in addition to the reversed "V" shaped progression electrical stimulus.

Figure 8A:
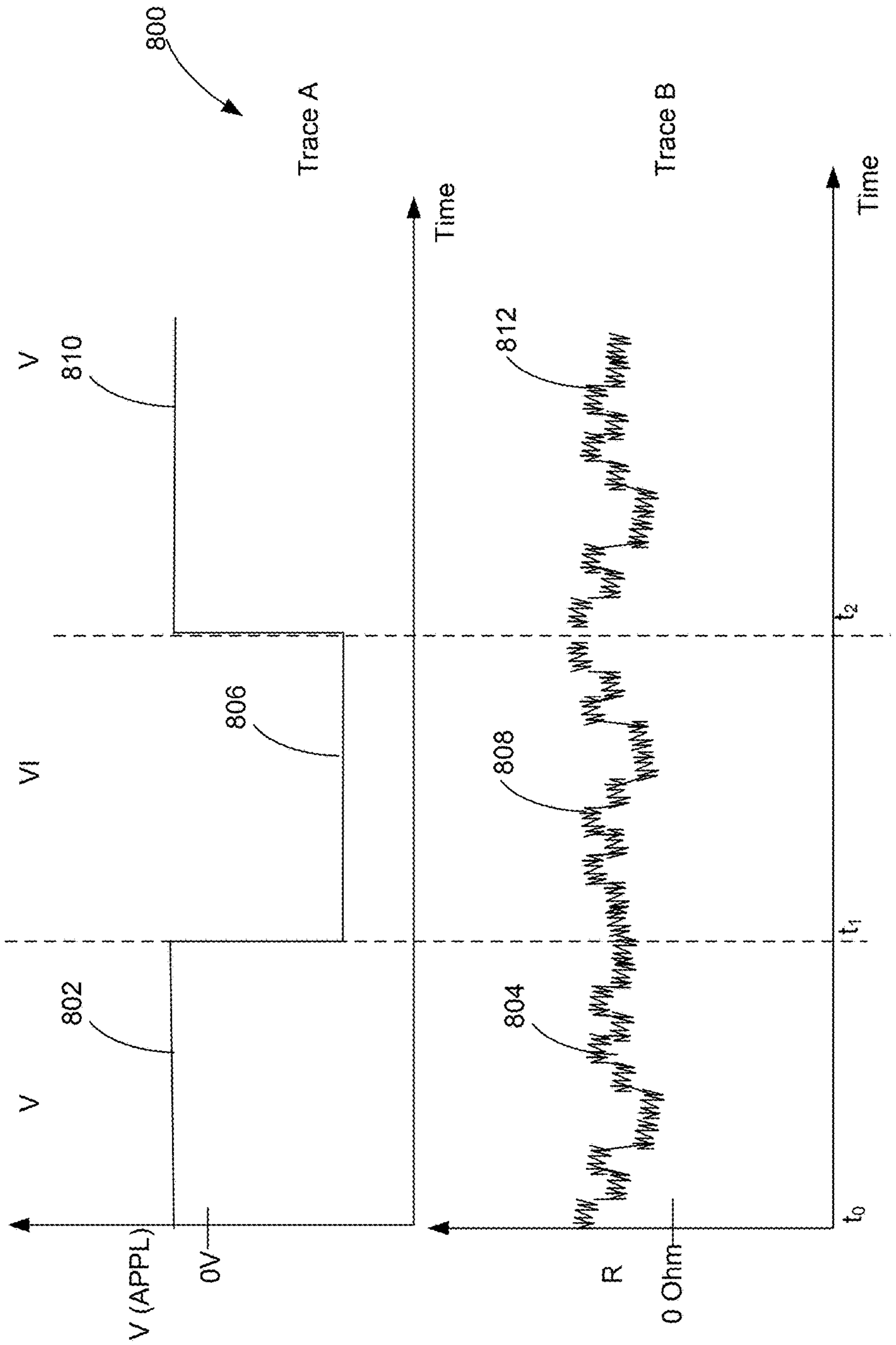
FIG. 8A is a schematic diagram illustrating an embodiment of a process for reversing the progression of a molecule in a nanopore.
Figure 8C:
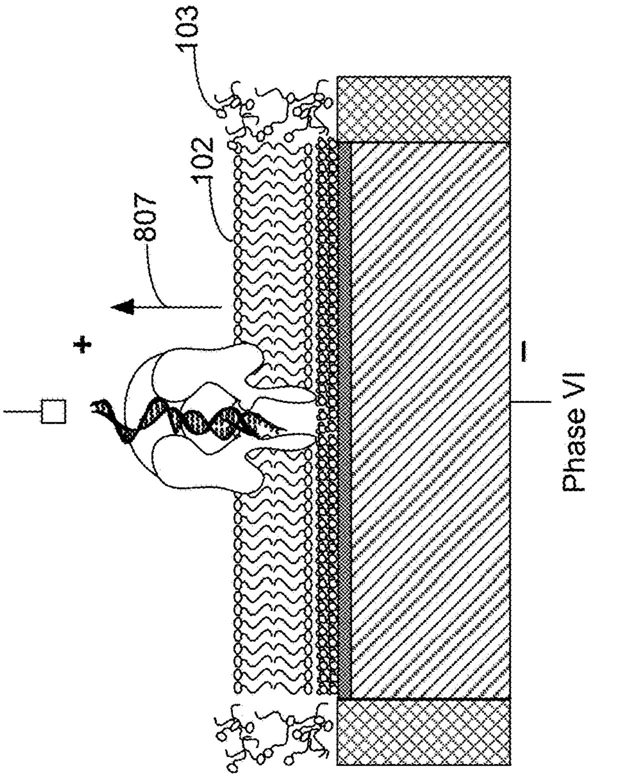
FIG. 8C illustrates phase VI during process 800.

FIG. 8 is a schematic diagram illustrating an embodiment of a process 800 for reversing the progression of a molecule in a nanopore of a nanopore device. In the example as illustrated, a dsDNA is analyzed using a αHL nanopore. Constant progression electrical stimuli and reverse progression electrical stimuli are used, and the electrical signature of the molecule is recorded continuously while the constant progression electrical stimuli and reverse progression electrical stimuli are applied and while the molecule is moving through the nanopore.

Although constant progression electrical stimuli are used in this example, various other types of progression electrical stimulus can be used. Examples of the various progression electrical stimulus are illustrated in FIGS. 6 and 8. Although constant reverse progression electrical stimuli are used in this example, various other types of reverse progression electrical stimulus can be used. The reverse progression electrical stimulus can include a ramp-up and/or a ramp-down and can include a smooth, square, "V", and/or "U" shaped profile similar to the progression electrical stimulus.

Trace A represents a voltage applied across the nanopore containing lipid bilayer. Trace B represents the resistance detected across the lipid nanopore containing bilayer. One or more steps of the process may be automated using hardware (e.g., integrated circuit) and/or execution of computer code.

At time $t_0$-$t_1$, a progression electrical stimulus 802 is applied across the lipid bilayer of the nanopore device, causing the dsDNA molecule to move in the direction of the applied electrical force 805 (Phase V, illustrated in FIG. 8B) as a resistance versus time profile 804 of the lipid bilayer is recorded.

At time $t_1$-$t_2$, a reverse progression electrical stimulus 806 is applied across the lipid bilayer. In this example, the reverse progression electrical stimulus 806 is an applied voltage level having a range of ~−50 mV to 100 mV. The natural tendency for the ssDNA molecule to re-associate to form a dsDNA drives the DNA molecule in the reverse direction 807 (Phase VI, illustrated in FIG. 8C). As the DNA molecule is pushed back through the nanopore in the reverse direction 807, ssDNA re-associates to form a dsDNA.

Figure 8B:
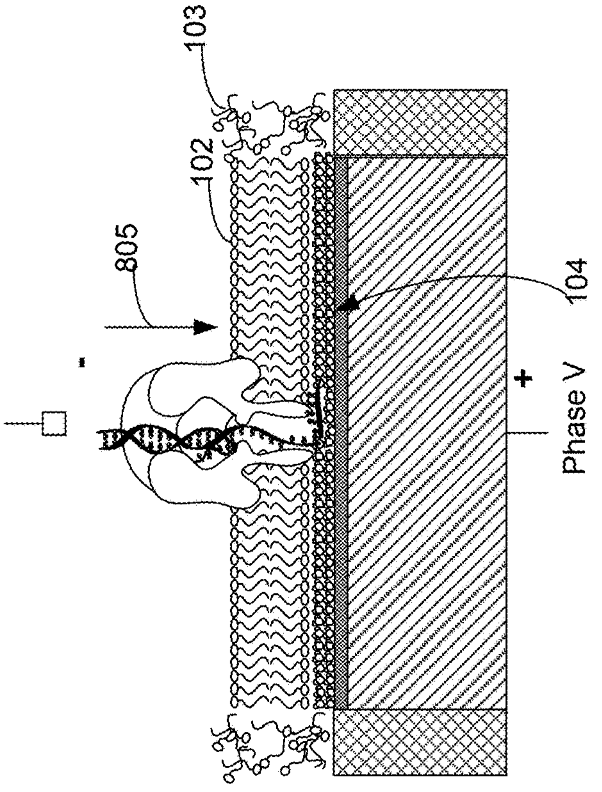
FIG. 8B illustrates phase V during process 800.

At time beyond $t_2$, a progression electrical stimulus 810 is again applied across the lipid bilayer, resuming the forward progression of the DNA molecule (Phase V, illustrated in FIG. 8B).

Figure 9:
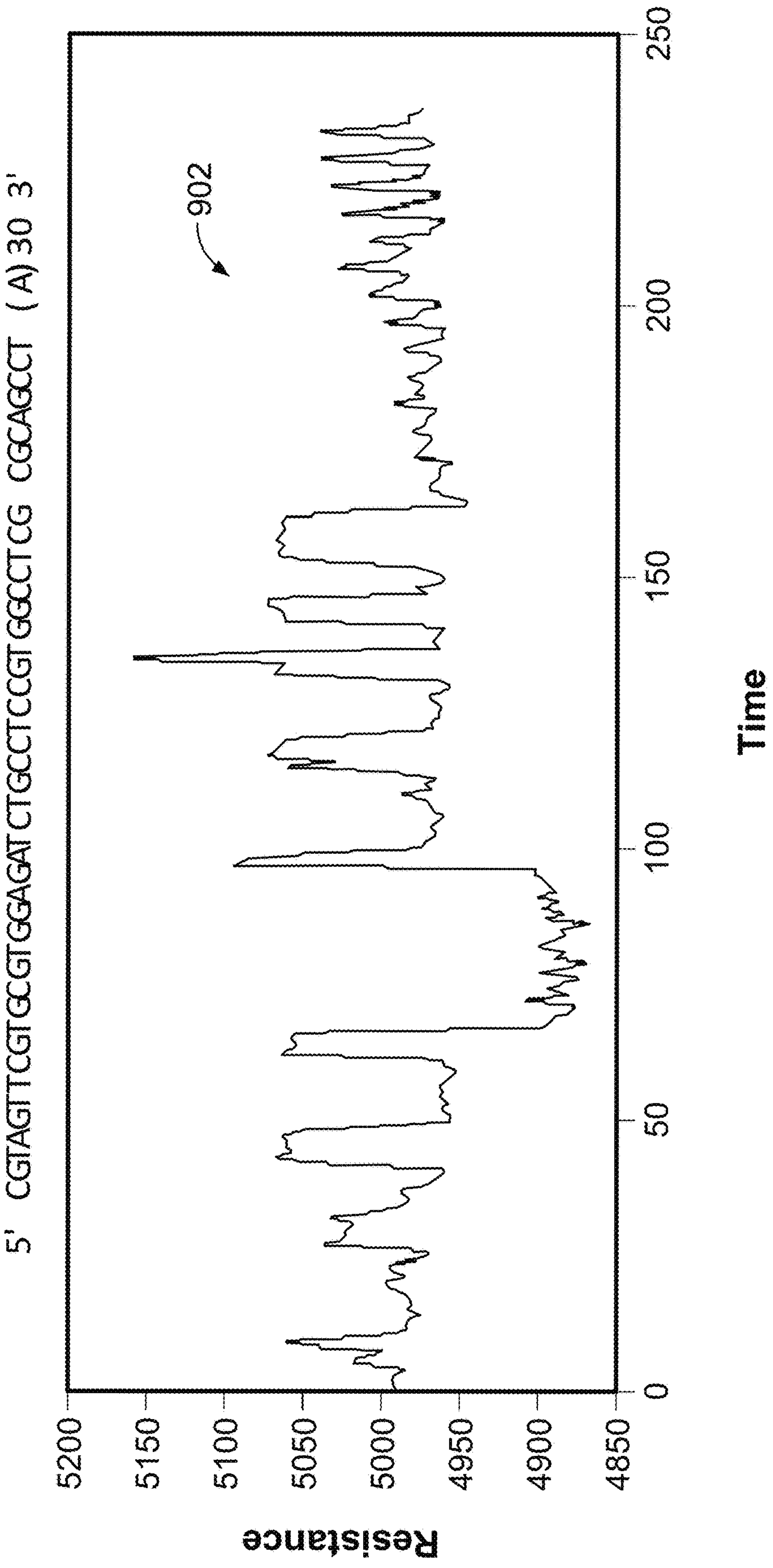
FIG. 9 is an embodiment of a resistance profile of a molecule driven through the nanopore.

FIG. 9 is example resistance versus time profile 902 detected as a single strand of a dsDNA molecule was threaded through a «HL nanopore using the techniques described herein. In the example shown, a constant progression electrical stimulus is applied to nanopore containing lipid bilayer, the electrical signature of the DNA molecule trapped in the nanopore is recorded continuously while the constant progression electrical stimulus is applied and while the DNA molecule is moving through the nanopore. The base sequence of the DNA molecule can be determined by comparing the detected resistance profile with the resistance profile(s) of known DNA sequence(s). For example, the base sequence of the DNA molecule may be determined to be that of a known DNA molecule if the resistance versus time profiles match. The various features of the profile, such as amplitude, frequency, edge rise (e.g., edge rise time), and/or edge fall (e.g., edge fall time) may be used to identify a particular DNA sequence.

Although the foregoing embodiments have been described in some detail for purposes of clarity of understanding, the invention is not limited to the details provided. There are many alternative ways of implementing the invention. The disclosed embodiments are illustrative and not restrictive.

Although electrical signatures expressed in terms of resistance versus time profile in the various embodiments described herein, it should be noted that the electrical signatures can also be expressed in terms of voltage versus time profile and/or current versus time profile in other embodiments. It should also be noted that an electrical property can be directly measured or indirectly measured. For example, resistance can be directly measured or indirectly measured by the voltage and/or the current, and current can be measured directly or indirectly measured by resistance and/or voltage. All ranges of electrical stimuli are given for a particular example nanopore system described herein. In other nanopore systems where chemistry is different, different ranges of electrical stimuli may apply.

What is claimed is:

1. A system for forming a nanopore in a membrane, the system comprising:

a chamber containing a nanopore forming solution, wherein the nanopore forming solution is deposited over a membrane; and a processor programmed to:

control application of a voltage stimulus to the membrane, wherein the voltage stimulus comprises a voltage stimulus amplitude;

control application of a measuring voltage stimulus to the membrane to determine whether the nanopore has been formed in the membrane;

measure a response to the measuring voltage stimulus, wherein the measuring voltage stimulus comprises a measuring voltage stimulus amplitude and wherein an absolute magnitude of the voltage stimulus amplitude is different from an absolute magnitude of the measuring voltage stimulus amplitude;

based on said measurement in response to the measuring voltage stimulus, detect whether a nanopore has been formed in the membrane; and in the event that a nanopore is not detected, iteratively initiating formation of a nanopore in the membrane by increasing the amplitude of the voltage stimulus applied to the membrane and detecting whether a nanopore has been formed in the membrane.

2. The system of claim 1, wherein the iteratively initiating formation of a nanopore in the membrane is repeated until formation of a nanopore is detected.

3. The system of claim 1, wherein the iteratively initiating formation of a nanopore in the membrane is repeated until the voltage stimulus has reached a predetermined maximum threshold.

4. The system of claim 1, wherein detection of whether a nanopore has been formed in the membrane comprises detecting a change in an electrical property of the membrane resulting from the formation of a nanopore in the membrane.

5. The system of claim 4, wherein said detecting a change in an electrical property of the membrane comprises detecting a change in a resistance of the membrane.

6. The system of claim 4, wherein said detecting whether a nanopore has been formed in the membrane comprises determining a number of nanopores formed in the membrane based on a size of change in the membrane electrical property.

7. The system of claim 6, wherein said processor is programmed to apply an erasing voltage stimulus to erase the membrane when it is determined that more than one nanopore is formed in the membrane.

8. The system of claim 1, wherein said processor is further programmed to apply a reverse oxidation stimulus to the membrane after the voltage stimulus is applied.

9. The system of claim 8, wherein the reverse oxidation stimulus has an opposite polarity to the voltage stimulus.

* * * * *